(12) United States Patent
McLeish et al.

(10) Patent No.: US 8,709,758 B2
(45) Date of Patent: Apr. 29, 2014

(54) METHODS AND COMPOSITIONS FOR INHIBITION OF NEUTROPHIL EXOCYTOSIS

(75) Inventors: Kenneth R. McLeish, Louisville, KY (US); Silvia M. Uriarte, Louisville, KY (US); Madhavi J. Rane, Prospect, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/056,521

(22) PCT Filed: Jul. 28, 2009

(86) PCT No.: PCT/US2009/051960
§ 371 (c)(1),
(2), (4) Date: Mar. 22, 2011

(87) PCT Pub. No.: WO2010/014608
PCT Pub. Date: Feb. 4, 2010

(65) Prior Publication Data
US 2011/0178020 A1    Jul. 21, 2011

Related U.S. Application Data

(60) Provisional application No. 61/084,110, filed on Jul. 28, 2008.

(51) Int. Cl.
*C12P 21/04* (2006.01)
*C12N 15/09* (2006.01)
*C12N 5/10* (2006.01)
*C07K 14/435* (2006.01)

(52) U.S. Cl.
USPC ...... 435/69.7; 435/320.1; 435/325; 536/23.4; 530/350

(58) Field of Classification Search
None
See application file for complete search history.

(56) References Cited

U.S. PATENT DOCUMENTS

| | | | |
|---|---|---|---|
| 4,736,866 | A | 4/1988 | Leder et al. |
| 4,870,009 | A | 9/1989 | Evans et al. |
| 5,166,320 | A | 11/1992 | Wu et al. |
| 6,645,501 | B2 | 11/2003 | Dowdy |
| 8,067,231 | B2 * | 11/2011 | Fernandez-Salas et al. .. 435/325 |
| 2002/0037524 | A1 | 3/2002 | Medlock et al. |
| 2003/0040038 | A1 | 2/2003 | Dowdy et al. |
| 2004/0253598 | A1 | 12/2004 | Baughn et al. |
| 2008/0064054 | A1 | 3/2008 | Fernandez-Salas et al. |

FOREIGN PATENT DOCUMENTS

WO   2006/073446 A2   7/2006

OTHER PUBLICATIONS

Mollinedo et al., Journal of Immunology, 177:2831-2841, 2006.*
Vaidyanathan et al., "The last exon of SNAP-23 regulates granule exocytosis from mast cells," J Biol Chem, 2001, vol. 276(27), pp. 25101-25106.
Wadia et al., "Transducible TAT-HA fusogenic peptide enhances escape of TAT-fusion proteins after lipid raft macropinocytosis," Nat Med, 2004, vol. 10(3), pp. 310-315.
Ward et al., "Priming of the neutrophil respiratory burst involves p38 mitogen-activated protein kinase-dependent exocytosis of flavocytochrome b558-containing granules," J Biol Chem, 2000, vol. 275(47), pp. 36713-36719.
Wilson et al., "Hepatocyte-directed gene transfer in vivo leads to transient improvement of hypercholesterolemia in low density lipoprotein receptor-deficient rabbits," J Biol Chem, 1992, vol. 267(2), pp. 963-967.
Wolff et al., "Direct gene transfer into mouse muscle in vivo," Science, 1990, vol. 247(4949 Pt 1), pp. 1465-1468.
Wu et al., Receptor-mediated gene delivery and expression in vivo, J Biol Chem, 1988, vol. 263(29), pp. 14621-14624.
Zelenin et al., Transfer of foreign DNA into the cells of developing mouse embryos by microprojectile bombardment, FEBS Lett, 1993, vol. 315(1), pp. 29-32.
Acsadi et al., "Human Dystrophin Expression in mdx Mice After Intramuscular Injection of DNA Constructs," Nature, 1991, vol. 352, pp. 815-818.
Becker-Hapak et al., "TAT-mediated protein transduction into mammalian cells," Methods, 2001, vol. 24(3), pp. 247-256.
Brown et al., "Distinct ligand-dependent roles of p38 MAPK in priming and activation of the neutrophil NADPH oxidase," J Biol Chem, 2004, vol. 279(26), pp. 27059-27068.
Burgoyne et al., Secretory granule exocytosis, Physiol Rev, 2003, vol. 83, pp. 581-632.
Chen et al., "SNARE-mediated membrane fusion," Nat Rev Mol Cell Biol, 2001, vol. 2(2), pp. 98-106.
Cheng et al., "In vivo promoter activity and transgene expression in mammalian somatic tissues evaluated by using particle bombardment," Proc Natl Acad Sci. USA., 1983, vol. 90(10), pp. 4455-4459.
Choi et al., Inhibition of NF-kappaB by a TAT-NEMO-binding domain peptide accelerates constitutive apoptosis and abrogates LPS-delayed neutrophil apoptosis, Blood, 2003, vol. 102, pp. 2259-2267.

(Continued)

*Primary Examiner* — Marianne P Allen
(74) *Attorney, Agent, or Firm* — Stites & Harbison PLLC; Terry L. Wright

(57) ABSTRACT

Isolated fusion polypeptides are provided that are comprised of a cell-penetrating polypeptide and a SNARE polypeptide aptamer. Further provided are methods for inhibiting neutrophil granule exocytosis that comprise contacting a neutrophil with a fusion polypeptide including a cell-penetrating polypeptide and a SNARE polypeptide aptamer such that the fusion polypeptide enters the neutrophil and inhibits neutrophil granule exocytosis. Also provided are methods for treating a neutrophil-mediated inflammatory disorder by inhibiting SNARE-associated exocytosis in neutrophils.

6 Claims, 12 Drawing Sheets

(56) References Cited

OTHER PUBLICATIONS

Coxon et al., "MAPK-activated protein kinase-2 participates in p38 MAPK-dependent and ERK-dependent functions in human neutrophils," Cell Signal, 2003, vol. 15(11), pp. 993-1001.
Coxon et al., Differential mitogen-activated protein kinase stimulation by Fc gamma receptor IIa and Fc gamma receptor IIIb determines the activation phenotype of human neutrophils, J Immunol, 2000, vol. 164, pp. 6530-6537.
Derossi et al., "The third helix of the Antennapedia homeodomain translocates through biological membranes," J. Bio. Chem., 1994, vol. 269, pp. 10444-10450.
Dewas et al., "TNF-α induces phosphorylation of p47phox in human neutrophils: Partial phosphorylation of p47phox is a common event of priming of human neutrophils by TNF-α and Granulocyte-Macrophage Colony-Stimulating Factor," J Immunol, 2003, vol. 171, pp. 4392-4398.
El-Benna et al., "Phagocyte NADPH oxidase: a multicomponent enzyme essential for host defenses," Arch Immunol Ther Exp, 2005, vol. 53, pp. 199-206.
Faurschou et al., "Neutrophil granules and secretory vesicles in inflammation," Microbes Infect, 2003, vol. 5(14), pp. 1317-1327.
Fawell et al., "Tat-mediated delivery of heterologous proteins into cells," Proc Natl Acad Sci USA, 1994, vol. 91(2), pp. 664-668.
Fleer R., "Engineering yeast for high level expression," Curr Opin Biotechnol, 1992, vol. 3(5), pp. 486-496.
Ferry et al., "Retroviral-mediated gene transfer into hepatocytes in vivo," Proc. Natl. Acad. Sci. USA, 1991, vol. 88 (19), pp. 8377-8381.
Frankel et al., "Cellular uptake of the tat protein from human immunodeficiency virus," Cell, 1988, vol. 55(6), pp. 1189-1193.
Galfre et al., "Preparation of monoclonal antibodies: strategies and procedures," Methods. Enzymol., 1981, vol. 73 (Pt B), pp. 3-46.
Gozal et al., "Proteomic analysis of CA1 and CA3 regions of rat hippocampus and differential susceptibility to intermittent hypoxiak" Neurochemistry, 2002, vol. 83, pp. 331-345.
Graham et al., "Characteristics of a human cell line transformed by DNA from human adenovirus type 5," J Gen Virol, 1977, vol. 36(1), pp. 59-74.
Guo et al., "Activator protein-1 activation in acute lung injury," Am J Pathol, 2002, vol. 161, pp. 275-282.
Han et al., "Critical role of the carboxyl terminus of praline-rich tyrosine kinases (Pyk2) in the activation of human neutrophils by tumor necrosis factor: separation of signals for the respiratory burst and degranulation," J Exp Med, 2003, vol. 197, pp. 63-75.
Haslett et al., "Modulation of multiple neutrophils functions by preparative methods or trace concentrations of bacterial lipopolysaccharide," Am J Pathol, 1985, vol. 119, pp. 101-110.
Herz et al., "Adenovirus-mediated transfer of low density lipoprotein receptor gene acutely accelerates cholesterol clearance in normal mice," Proc Natl Acad Sci USA, 1993, vol. 90(7), pp. 2812-2816.
Hong W., "SNAREs and traffic," Biochimica et Biophysica Acta, 2005, vol. 1744, pp. 120-144.
Kay et al., "Hepatic gene therapy: persistent expression of human alpha 1-antitrypsin in mice after direct gene delivery in vivo," Hum Gene Ther, 1992, vol. 3(6), pp. 641-647.
Lentsch et al., "Regulation of acute lung inflammatory injury by endogenous IL-13," J Immunol, 1999, vol. 162, pp. 1071-1076.
Lominadze et al., "Proteomic analysis of human neutrophil granules," Mol Cell Proteomics, 2005, vol. 4(10), pp. 1503-1521.
Lominadze et al., "Myeloid-related protein-14 is a p38 MAPK substrate in human neutrophils," J Immunol, 2005, vol. 174, pp. 7257-7267.
Lu et al., "Mediation of endothelial cell damage by serine proteases, but not superoxide, released from antineutrophil cytoplasmic antibody-stimulated neutrophils," Arthritis Rheum, 2006, vol. 54, pp. 1619-1628.
Martin-Martin et al., "Involvement of SNAP-23 and syntaxin 6 in human neutrophil exocytosis," Blood, 2000, vol. 96, pp. 2574-2583.
McLeish et al., "Activation of mitogen-activated protein kinase cascades during priming of human neutrophils by TNF-α and GM-CSF," J Leukoc Biol, 1998, vol. 64, pp. 537-545.
Mollinedo et al., "Role of Vesicle-Associated Membrane Protein-2, through Q-soluble N-ethylmaleimide-sensitive factor attachment protein receptor/R-soluble N-ethylmaleimide-sensitive factor attachment protein receptor interaction, in the exocytosis of specific and tertiary granules of human neutrophils," J Immunol, 2003, vol. 170, pp. 1034-1042.
Mollineddo et al., "Identification of two isoforms of the vesicle-membrane fusion protein SNAP-23 in human neutrophils and HL-60 cells," Biochem Biophys Res Commun, 1997, vol. 231, pp. 808-812.
Mulligan et al., "Role of B2 integrins of rat neutrophils in complement- and oxygen radical-mediated acute inflammatory injury," J Immunol, 1992, vol. 148, pp. 1847-1857.
Nakamura et al., "Monoclonal antibody 7D5 raised to cytochrome b558 of human neutrophils: immunocytochemical detection of the antigen in peripheral phagocytes of normal subjects, patients with chronic granulomatous disease, and their carrier mothers," Blood, 1987, vol. 69(5), pp. 1404-1408.
Powell et al., "Proteomic identification of 14-3-3ζ as a mitogen-activated protein kinase-activated protein kinase 2 substrate: role of dimmer formation and ligand binding," Mol Cell Biol, 2003, vol. 23(15), pp. 5376-5387.
Prochiantz A., "Messenger proteins: homeoproteins, TAT and others," Curr Opin Cell Biol, 2000, vol. 12, pp. 400-406.
Rane et al., "γ-Amino butyric acid type B receptors stimulate neutrophil chemotaxis during ischemia-reperfusion," J Immunol, 2005, vol. 174, pp. 7242-7249.
Rane et al., "Heat shock protein 27 controls apoptosis by regulating Akt activation," J Biol Chem, 2003, vol. 278, pp. 27828-27835.
Rea et al., "Syndet, an adipocyte target SNARE involved in the insulin-induced translocation of GLUT4 to the cell surface," J Biol Chem, 1998, vol. 273(30), pp. 18784-18792.
Rosenfeld et al., "In vivo transfer of the human cystic fibrosis transmembrane conductance regulator gene to the airway epithelium," Cell, 1992, vol. 68, pp. 143-155.
Schwarze et al., "Protein transduction: unrestricted delivery into all cells?" Trends Cell Biol, 2000, vol. 10(7), pp. 290-295.
Schwarze et al., "In vivo protein transduction: delivery of a biologically active protein into the mouse," Science, 1999, vol. 285 (5433), pp. 1569-1572.
Sheppard et al., "Structural organization of the neutrophil NADPH oxidase: phosphorylation and translocation during priming and activation," J Leukoc Biol, 2005, vol. 78(5), pp. 1025-1042.
Shukla et al., "Identification of three new splice variants of the SNARE protein SNAP-23," Biochem Biophys Res Commun, 2001, vol. 285(2), pp. 320-327.
Stewart et al., "Cell-penetrating peptides as delivery vehicles for biology and medicine," Org Biomol Chem, 2008, vol. 6(13), pp. 2242-2255.
Teng et al., "The syntaxins," Genome Biol, 2001, vol. 2 (11), Reviews 3012.1-3012.7.
Uriarte et al., "Akt inhibition upregulates FasL, downregulates c-FLIPs and induces caspase-8 dependent cell death in Jurkat T lymphocytes," Cell Death and Differentiation, 2005, vol. (3), pp. 233-242.
Urlab et al., "Isolation of Chinese hamster cell mutants deficient in dihydrofolate reductase activity," Proc. Natl. Acad. Sci. USA., 1980, vol. 77, pp. 4216-4220.

\* cited by examiner

US 8,709,758 B2

METHODS AND COMPOSITIONS FOR INHIBITION OF NEUTROPHIL EXOCYTOSIS

RELATED APPLICATIONS

This application claims priority from U.S. Provisional Application Ser. No. 61/084,110, filed Jul. 28, 2008, the entire disclosure of which is incorporated herein by this reference.

GOVERNMENT INTEREST

This invention was made with Government support under grants AI075212, AI007958 and HL087924 awarded by the National Institutes of Health. The Government has certain rights in this invention.

TECHNICAL FIELD

The presently-disclosed subject matter relates to compositions and methods of using the same for inhibiting neutrophil exocytosis. In particular, the presently-disclosed subject matter relates to fusion polypeptides comprising a cell-penetrating polypeptide, which facilitates entry of the fusion polypeptide into a neutrophil, and a SNARE polypeptide aptamer, which inhibits SNARE-associated exocytosis in a neutrophil.

BACKGROUND

Neutrophils are the primary cellular component of innate immunity. To prevent unwanted damage to normal tissue, circulating neutrophils are normally poorly responsive to extracellular stimuli. However, to allow appropriate responses to invading bacteria or other inflammatory stimuli, neutrophils undergo a series of phenotypic changes. First, neutrophils are converted from benign cells, capable of circulating without inducing tissue injury, to cells that are primed for an enhanced response. Second, the primed neutrophils are activated to migrate into tissue and generate and release toxic agents capable of killing bacteria or injuring normal cells.

For example, during neutrophil clearance of invading microorganisms, the neutrophils undergo a step-wise conversion from quiescent circulating cells to activated cells capable of producing large quantities of reactive oxygen species (ROS) and releasing bactericidal proteins (1). Neutrophil priming is an intermediate step in this activation process, whereby exposure to pro-inflammatory cytokines and chemokines; such as tumor necrosis factor (TNF)-α, granulocyte macrophage-colony stimulating factor (GM-CSF), interleukin (IL)-8, and platelet activating factor (PAF); enhance neutrophil responses, including the generation of ROS, to a second stimulus, such as the bacterial wall component N-formyl-methionyl-leucyl-phenylalanine (fMLP) (3).

The enzyme responsible for ROS production in neutrophils is the NADPH oxidase; a multicomponent enzyme with components located in the plasma membrane, in the cytosol, and in the membranes of all neutrophil granule subsets (2). The membrane component of NADPH oxidase is a cytochrome b558, a heterodimer composed of gp22phox and gp91phox, and the cytosolic components are p47phox, p67phox, p40phox and the small G-protein Rac2 (3). The production of ROS is normally tightly regulated. However, excessive or inappropriate ROS generation due to enhanced neutrophil priming and activation can lead to injury to normal tissue.

Evidence indicates that neutrophil priming and activation results, at least in part, from exocytosis of intracellular granules from neutrophils. Priming agents, such as TNF-α and PAF, induce exocytosis of neutrophil granules and result in increased plasma membrane expression of gp91phox and gp22phox (2, 3). It has recently been demonstrated that all granules contain gp91phox and gp22phox in their membranes, indicating that exocytosis of each of the neutrophil granules enhances this plasma membrane expression (4). Additionally, it was shown that p38 MAPK regulated neutrophil granule exocytosis in response to TNF-α and lipopolysaccharide (LPS) (5), providing an explanation for the previously recognized role of p38 MAPK in neutrophil priming (6, 7).

Priming enhances the ability of neutrophils to produce ROS and to kill bacteria. However, excessive or inappropriate activation of neutrophils and enhanced generation of ROS also contributes to tissue damage, such as that seen in ischemia-reperfusion injury (I/R) of the heart, brain, and kidneys; anti-neutrophil cytoplasmic antibody (ANCA)-associated vasculitis; rheumatoid arthritis; acute glomerulonephritis; the lung injury of sepsis; and other disorders involving neutrophil-mediated inflammatory processes. Indeed, neutrophils have been shown to mediate damage to postcapillary venules during I/R injury, and have thus been implicated in the pathogenesis of, for example, myocardial infarction, stroke, and acute tubular necrosis. Additionally, neutrophils have been shown to directly injure vascular endothelial cells and are one of the cell types contributing to the formation of glomerular crescents in ANCA-associated vasculitis.

In any event, despite extensive research into neutrophil activation and priming, and the role of neutrophils in inflammatory processes, current therapies directed toward inhibiting detrimental neutrophil-mediated inflammation are less than sufficient. None of the known therapeutic agents or treatment modalities provide a sufficient therapeutic approach whereby neutrophil exocytosis can be inhibited, and undesirable neutrophil-mediated inflammation and subsequent cellular and tissue damage can be reduced.

SUMMARY

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, an isolated fusion polypeptide is provided that inhibits soluble N-ethylmaleimide-sensitive factor attachment protein receptor (SNARE)-associated exocytosis in neutrophils. In some embodiments, the fusion polypeptide comprises a cell-penetrating polypeptide and a SNARE polypeptide aptamer selected from the polypeptides provided in SEQ ID NOS: 1 and 18. In some embodiments, the cell-penetrating polypeptide comprises a human immunodeficiency virus transactivator of transcription (TAT), a penetratin, an HSV VP22, a polyarginine, a pep-1, or a transportan polypeptide. In some embodiments, the cell-penetrating polypeptide is a TAT polypeptide of SEQ ID NO: 5.

With respect to the SNARE polypeptide aptamers of the presently-disclosed fusion polypeptides, in some embodiments, the SNARE polypeptide aptamer comprises a syntaxin 4 polypeptide fragment, such as the one provided in SEQ ID NO: 18. In other embodiments, the SNARE polypeptide aptamer comprises a (SNAP)-23 polypeptide, such as the one provided in SEQ ID NO: 1. In some embodiments, the SNARE polypeptide aptamer comprises a polypeptide of SEQ ID NO: 1 and the cell-penetrating polypeptide comprises a polypeptide of SEQ ID NO: 5. In some embodiments, the fusion polypeptide can further comprise an affinity tag, such as a hemagglutinin polypeptide.

Further provided, in some embodiments of the presently-disclosed subject matter, are isolated nucleic acids that include a nucleotide sequence encoding a fusion polypeptide that comprises a cell-penetrating polypeptide and a SNARE polypeptide aptamer in accordance with the presently-disclosed subject matter. In some embodiments, a nucleic acid sequence is provided that comprises the sequence of SEQ ID NO: 11. In some embodiments, a nucleic acid sequence is provided that encodes a fusion polypeptide comprising a SNARE polypeptide aptamer of SEQ ID NO: 1 and a cell-penetrating peptide of SEQ ID NO: 5.

In some embodiments, a vector is provided that includes a nucleic acid of the presently-disclosed subject matter. In some embodiments of the presently-disclosed vectors, the nucleic acid is operatively linked to an expression cassette. Further, in some embodiments, cells are provided that comprise a nucleotide sequence encoding a fusion polypeptide of the presently-disclosed subject matter.

Still further provided, in some embodiments of the presently-disclosed subject matter, are methods for inhibiting neutrophil granule exocytosis. In some embodiments, a method for inhibiting neutrophil granule exocytosis is provided that comprises contacting a neutrophil with a fusion polypeptide of the presently-disclosed subject matter, such that the fusion polypeptide enters the neutrophil and inhibits SNARE-associated neutrophil granule exocytosis. In some embodiments of the methods for inhibiting neutrophil granule exocytosis, the neutrophil is contacted with a concentration of the fusion polypeptide of above about 0.5 µg/ml to thereby inhibit neutrophil granule exocytosis. In some embodiments, the fusion polypeptide inhibits exocytosis of a secretory vesicle, a specific granule, or a gelatinase granule. In some embodiments, the fusion polypeptide inhibits neutrophil granule exocytosis by inhibiting the formation of a trans-SNARE complex, by inhibiting SNARE-dependent granule fusion, or both.

Also provided, in some embodiments of the presently-disclosed subject matter, are methods for treating a neutrophil-mediated inflammatory disorder in a subject. In some embodiments, a therapeutic method is provided that comprises administering to a subject an effective amount of a fusion polypeptide of the presently-disclosed subject matter such that the fusion polypeptide inhibits SNARE-associated exocytosis in neutrophils to thereby treat the neutrophil-mediated inflammatory disorder. In some embodiments, the fusion polypeptide can be administered to the subject by intravenous injection. In some embodiments, the inflammatory disorder can be selected from rheumatoid arthritis, acute gouty arthritis, acute glomerulonephritis, acute transplant rejection, traumatic brain and spinal cord injury, vasculitis, ischemia-reperfusion injury, acute lung injury associated with sepsis, and immune complex-mediated lung injury.

Advantages of the presently-disclosed subject matter will become evident to those of ordinary skill in the art after a study of the description, Figures, and non-limiting Examples in this document.

BRIEF DESCRIPTION OF THE DRAWINGS

(FIG. 5C), and treated with 5 µg/ml of a TAT-HA-SNAP-23 peptide after a 30 min incubation at 37° C. (FIG. 5D). A mouse HA antibody was used to identify the peptides and AlexaFluor® 546 dye was used to stain the cells.

BRIEF DESCRIPTION OF THE SEQUENCE LISTING

Figure 1:
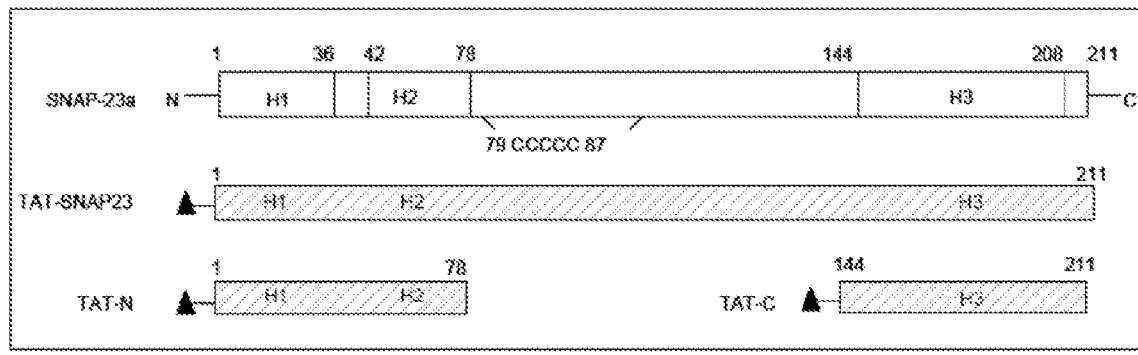
FIG. 1 is a schematic diagram depicting exemplary SNAP-23 polypeptides expressed as a human immunodeficiency virus transactivator of transcription (TAT) fusion polypeptide, where the triangle and stick represent the TAT sequence and a hemagglutinin tag, the heptad repeat regions are indicated by H, the palmitoylate site of SNAP-23 is represented by five cysteine residues, and the numbers correspond to the amino acid positions.

SEQ ID NO: 1 is an amino acid sequence of a SNAP-23 polypeptide that includes 78 amino acids from the N-terminus of the full-length human SNAP-23 protein.

SEQ ID NO: 2 is an amino acid sequence of a SNAP-23 polypeptide that includes 40 amino acids from the N-terminus of the full-length human SNAP-23 protein.

SEQ ID NO: 3 is an amino acid sequence of a SNAP-23 polypeptide that includes 60 amino acids from the C-terminus of the full-length human SNAP-23 protein.

SEQ ID NO: 4 is an amino acid sequence of a SNAP-23 polypeptide that includes 24 amino acids from the C-terminus of the full-length human SNAP-23 protein.

SEQ ID NO: 5 is an amino acid sequence of a human immunodeficiency virus transactivator of transcription (TAT) cell-penetrating polypeptide.

SEQ ID NO: 6 is an amino acid sequence of a penetratin cell-penetrating polypeptide.

SEQ ID NO: 7 is an amino acid sequence of a HSV VP22 cell-penetrating polypeptide.

SEQ ID NO: 8 is an amino acid sequence of a polyarginine cell-penetrating polypeptide.

SEQ ID NO: 9 is an amino acid sequence of a pep-1 cell-penetrating polypeptide.

SEQ ID NO: 10 is an amino acid sequence of a transportan cell-penetrating polypeptide.

SEQ ID NO: 11 is a nucleic acid sequence encoding an exemplary fusion polypeptide comprised of a TAT cell-penetrating polypeptide, a hemagglutinin affinity tag, and a SNAP-23 polypeptide aptamer from the amino-terminus of SNAP-23 (TAT-HA-SNAP-23).

SEQ ID NO: 12 is an amino acid sequence of an exemplary TAT-HA-SNAP-23 fusion polypeptide.

SEQ ID NO: 13 is an amino acid sequence of an exemplary hemagglutinin affinity tag.

SEQ ID NO: 14 is a nucleic acid sequence of a forward RT-PCR primer used to amplify a full-length SNAP-23 nucleic acid sequence from human neutrophil RNA.

SEQ ID NO: 15 is a nucleic acid sequence of a reverse RT-PCR primer used to amplify a full-length SNAP-23 nucleic acid sequence from human neutrophil RNA.

SEQ ID NO: 16 is a nucleic acid sequence of a reverse RT-PCR primer used to amplify a portion of a SNAP-23 nucleic acid sequence, corresponding to the amino-terminus of SNAP-23, from human neutrophil RNA.

SEQ ID NO: 17 is a nucleic acid sequence of a forward RT-PCR primer used to amplify a portion of a SNAP-23 nucleic acid sequence, corresponding to the carboxy-terminus of SNAP-23, from human neutrophil RNA.

SEQ ID NO: 18 is an amino acid sequence of a syntaxin 4 polypeptide aptamer.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The term "isolated", when applied to a nucleic acid or polypeptide, denotes that the nucleic acid or polypeptide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A polypeptide that is the predominant species present in a preparation is substantially isolated. The term "isolated" further denotes that a nucleic acid or polypeptide gives rise to essentially one band in an electrophoretic gel. Particularly, it means that the nucleic acid or polypeptide is in some embodiments at least about 50% pure, in some embodiments at least about 85% pure, and in some embodiments at least about 99% pure.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long.

A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g., degenerate variants, including degenerate codon substitutions) and complementary sequences and as well as the sequence explicitly indicated.

The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer, et al. (1991) *Nucleic Acid Res* 19:5081; Ohtsuka et al. (1985) *J Biol Chem* 260:2605 2608; Rossolini et al. (1994) *Mol Cell Probes* 8:91 98).

Exocytosis in neutrophils occurs in sequential stages, starting with disassembly of the cortical actin cytoskeleton and granule recruitment to the plasma membrane, where tethering and docking of granules are mediated by specific proteins.

This tethering and docking of the granules to specific proteins is then followed by membrane fusion and release of an assortment of granules, including specific, secretory, azurophil, and gelatinase granules, as well as their related contents into the extracellular media (8).

Soluble N-ethylmaleimide-sensitive factor attachment protein receptors ("SNAREs" or "SNAP receptors") perform a central role in neutrophil exocytosis by mediating granule docking and membrane fusion. SNAREs are classified based on whether a conserved glutamine (Q) or arginine (R) residue is present in their SNARE-interaction motif (9), an amino acid domain in the SNAREs that mediates the association of the various SNARE proteins into a core complex capable of mediating granule docking and membrane fusion. The SNARE hypothesis proposes that a syntaxin protein provides one Q-containing helix, a soluble N-ethylmaleimide-sensitive factor attachment protein-23/25 (SNAP-23/25) contributes two Q-containing helices, and a vesicle-associated membrane protein (VAMP) contributes one R-containing helix to a coiled-coil trans-SNARE complex (10). This 3Q:1R helix allows specific SNARE pairing and provides the energy for membrane fusion between the vesicle and the target membrane (10).

SNAP-23 is a SNAP-25 homolog that is expressed in non-neuronal tissue, and, at the mRNA level, five SNAP-23 isoforms have been reported in eosinophils, basophils, neutrophils and peripheral blood mononuclear cells (11). In human neutrophils, SNAP-23a is the major form of this SNARE protein that is expressed (12). SNAP-23 has been specifically detected on gelatinase granules, specific granules, and the plasma membrane (4). Others (13) have shown that the introduction of antibodies against SNAP-23 and syntaxin 6 into neutrophils by electroporation was capable of inhibiting specific and azurophilic granule exocytosis stimulated by guanosine gamma thio-phosphate (GTPγS). Similarly, other studies (14) have shown that introduction of anti-syntaxin 4 antibodies into neutrophils by electroporation was capable of inhibiting specific and gelatinase granule exocytosis stimulated by $Ca^{2+}$ and GTPγS. As such, SNAP-23, syntaxin 4, and syntaxin 6 are potential targets for inhibition of exocytosis of neutrophil granule subsets. To that end, the presently-disclosed subject matter provides new compositions, and methods of using the same, for inhibiting neutrophil exocytosis.

In some embodiments of the presently-disclosed subject matter, compositions are provided that comprise isolated polypeptides for inhibiting exocytosis of neutrophil granules, and thereby decreasing detrimental neutrophil-mediated inflammatory responses. In some embodiments, an isolated fusion polypeptide is provided that comprises a cell-penetrating polypeptide, which facilitates entry of the fusion polypeptide into a neutrophil, and a SNARE polypeptide aptamer, which blocks the interaction of cognate SNARE partners and thereby inhibits SNARE-associated exocytosis in neutrophils.

One aspect of the presently-disclosed subject matter thus pertains to fusion proteins and nucleic acids (e.g., DNA) encoding the fusion proteins. The term "fusion protein" is intended to describe at least two polypeptides, typically from different sources, which are operatively linked. With regard to the polypeptides, the term "operatively linked" is intended to mean that the two polypeptides are connected in a manner such that each polypeptide can serve its intended function. Typically, the two polypeptides are covalently attached through peptide bonds and can be produced by standard recombinant or chemical synthesis techniques. For example, using recombinant techniques, a DNA molecule encoding a first polypeptide can be ligated to another DNA molecule encoding the second polypeptide, and the resultant hybrid DNA molecule can be expressed in a host cell to produce the fusion protein. The DNA molecules are generally ligated to each other in a 5' to 3' orientation such that, after ligation, the translational frame of the encoded polypeptides is not altered (i.e., the DNA molecules are ligated to each other in-frame).

In some embodiments, the fusion polypeptides of the presently-disclosed subject matter are comprised, in part, of a first polypeptide, referred to as a cell-penetrating polypeptide. The term "cell-penetrating polypeptide" is used herein to refer to polypeptides that have the ability to provide entry of a coupled peptide into a cell. Exemplary cell-penetrating polypeptides that can be used in accordance with the presently-disclosed subject matter include, but are not limited to: a human immunodeficiency virus transactivator of transcription (TAT) polypeptide (Frankel, A. D., & Pabo, C. (1988), Cell, 55:1189-1193; Fawell, S., et al., (1994) PNAS USA, 91:664-8; Becker-Hapak, M. et al. (2001), Methods, 24(3): 247-56; Schwarze S. R. et al. (2000), Trends Cell Biol., 10(7): 290-5; Matsushita, K. et al. (2005), Mol. Pharm., 67(4):1137-44; U.S. Pat. No. 6,645,501; and U.S. Patent Application Publication No. 2003/0040038); an Antennapedia homeodomain polypeptide, referred to as "penetratin" (e.g., AKI-WFQNRRMKWKKEN; SEQ ID. NO: 6) (Derossi et al., (1994), J. Bio. Chem., 269:10444-10450); an HSV VP22 polypeptide (SEQ ID NO: 7) (Elliot and O'Hare. (1997), Cell. 88:223-234); a polyarginine polypeptide (e.g., RRRRRRRR; SEQ ID NO: 8); a pep-1 polypeptide (KETWWETWWTEWSQPKKKRKV; SEQ ID NO: 9); and a transportan polypeptide (GWTLNSAGYLLGKINLKA-LAALAKKIL; SEQ ID NO: 10) (Stewart et al., (2008), Org. Biomol. Chem. 6, 2242-2255). In some embodiments, the cell-penetrating peptide thus comprises a TAT, penetratin, HSV VP22, a polyarginine, a pep-1, or a transportan polypeptide. In some embodiments, the cell-penetrating polypeptide is a TAT polypeptide and has the following amino acid sequence: YGRKKRRQRRR (SEQ ID NO: 5). In some embodiments, the cell-penetrating polypeptide can be flanked by glycine residues to allow for free rotation.

In some embodiments, the first polypeptide of the fusion protein is operatively linked to a second polypeptide, which is a SNARE polypeptide aptamer. The term "aptamer" is used herein to refer to a fragment of an endogenous protein that is capable of binding to cognate protein binding sites and preventing interaction with target molecules. For example, in some embodiments, the SNARE polypeptide aptamer selectively binds a SNARE-interaction motif of a target SNARE protein such that the SNARE polypeptide aptamer inhibits binding of other SNARE proteins to the target SNARE protein, and thereby inhibits the formation of a trans-SNARE complex.

In some embodiments, the SNARE polypeptide aptamer comprises a SNAP-23 amino-terminus polypeptide fragment or a syntaxin 4 polypeptide fragment. In some embodiments, the SNARE polypeptide aptamer comprises a syntaxin 4 polypeptide fragment, such as the one provided in SEQ ID NO: 18. In other embodiments, the SNARE polypeptide aptamer is a polypeptide fragment from the amino-terminus of SNAP-23 (e.g., human SNAP-23; GENBANK® Accession No. NP_003816), such as the polypeptide provided in SEQ ID NO: 1. In some embodiments, the SNARE polypeptide aptamer comprises a polypeptide of SEQ ID NO: 1 and the cell-penetrating polypeptide comprises a polypeptide of SEQ ID NO: 5.

TABLE 1

Exemplary SNARE Polypeptide Aptamer Sequences

SEQ ID NO: 1-78 AA N-terminus of human SNAP-23:

M D N L S S E E I Q Q R A H Q I T D E S L E S T R

R I L G L A I E S Q D A G I K T I T M L D E Q K E

Q L N R I E E G L D Q I N K D M R E T E K T L T E

L N K

SEQ ID NO: 18-68 AA polypeptide from human Syntaxin 4:

V T R Q A L N E I S A R H S E I Q Q L E R S I R E L

H D I F T F L A T E V E M Q G E M I N R I E K N I

L S S A D Y V E R G Q E H V K T A

The terms "N-terminus" or "amino-terminus" and "C-terminus" or "carboxyl-terminus" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide. Where amino-terminus or carboxyl-terminus refer to an entire polypeptide or polypeptide fragment, the terms refer to one or more amino acids at amino or carboxyl ends, respectively, of the polypeptide or the polypeptide fragment.

In some embodiments of the presently-disclosed SNARE polypeptide aptamers, one or more amino acid residues can be deleted from the amino-terminus, the carboxyl terminus, or from both ends of the polypeptide fragments. For example, in some embodiments, about 1, about 2, about 3, about 4, about 5, about 6, about 7, about 8, about 9, or about 10 amino acids can be deleted from the amino-terminus or the carboxyl-terminus of the polypeptide fragments provided in SEQ ID NOS: 1 or 18. In some embodiments, about 1, about 2, about 3, about 4, about 5, about 6, about 7, about 8, about 9, or about 10 amino acids can be independently deleted from the amino-terminus and the carboxyl-terminus of the polypeptide fragments provided in SEQ ID NOS: 1 or 18.

As noted, to operatively link the first and second polypeptides, nucleotide sequences encoding the first and second polypeptides are ligated to each other in-frame to create a chimeric gene encoding a fusion polypeptide. In some embodiments, a further nucleic acid sequence encoding an additional polypeptide sequence can be incorporated between the nucleotide sequences encoding the first and second polypeptides. For example, in some embodiments, a fusion polypeptide can be provided that contains an operatively-linked polypeptide, such as an affinity tag, that is positioned between the first and second polypeptides, i.e., [cell-penetrating polypeptide]-[affinity tag]-[SNARE polypeptide aptamer].

The term "affinity tag" is used herein to denote a polypeptide segment that can be attached to a one or more polypeptides to provide for purification or detection of the one or more polypeptides. In principal, any peptide or protein for which an antibody or other specific binding agent is available can be used as an affinity tag. Affinity tags include, but are not limited to: a poly-histidine tract, protein A (Nilsson et al., EMBO J. 4:1075, 1985; Nilsson et al., Methods Enzymol. 198:3, 1991), glutathione S transferase (Smith and Johnson, Gene 67:31, 1988), Glu-Glu affinity tag (Grussenmeyer et al., Proc. Natl. Acad. Sci. USA 82:7952-4, 1985), substance P, streptavidin binding peptide, or other antigenic epitope, such as a hemagglutinin (HA) polypeptide. See, in general, Ford et al., Protein Expression and Purification 2: 95-107, 1991.

In some embodiments, a fusion polypeptide is provided that comprises an HA polypeptide, such as the polypeptide set forth in SEQ ID NO: 13, as an affinity tag. In some embodiments, a fusion polypeptide is provided that is comprised of an HA polypeptide positioned between a TAT cell-penetrating polypeptide and a SNAP-23 aptamer, such as the polypeptide set forth in SEQ ID NO: 12.

In some embodiments of the presently-disclosed subject matter, isolated nucleic acids are further provided that comprise a nucleotide sequence encoding a fusion polypeptide that inhibits SNARE-associated exocytosis in neutrophils. In some embodiments, an isolated nucleic acid is provided that encodes a fusion polypeptide comprising a cell-penetrating polypeptide and a SNARE polypeptide aptamer, which is selected from a SNAP-23 amino-terminus polypeptide fragment, such as the one provided in SEQ ID NO: 1, or a syntaxin 4 polypeptide fragment, such as the one provided in SEQ ID NO: 18. In some embodiments, a nucleic acid sequence is provided that comprises the sequence of SEQ ID NO: 11. In some embodiments, a nucleic acid sequence is provided that encodes a SNARE polypeptide aptamer of SEQ ID NO: 1 and a cell-penetrating peptide of SEQ ID NO: 5.

To generate an exemplary fusion polypeptide in accordance with the presently-disclosed subject matter, in some embodiments, the nucleic acid encoding the fusion polypeptide is inserted into an appropriate expression vector that contains the necessary elements for the transcription and translation of the inserted protein-coding sequence. A variety of host-vector systems can be utilized to express an inserted protein-coding sequence, including mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements can be used. As one exemplary embodiment of a vector comprising a nucleic acid sequence of the presently disclosed subject matter, an exemplary vector can be a plasmid, such as the plasmid pTAT-HA, into which a nucleic acid encoding an SNARE polypeptide aptamer can be cloned by the use of internal restriction sites present within the vector.

In some embodiments, the nucleic acids of the presently-disclosed subject matter are operably linked to an expression cassette. The terms "associated with", "operably linked", and "operatively linked," when used herein in reference to a nucleic acid sequence, refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, and comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

Once generated by an appropriate host-vector system, the fusion polypeptides can then be separated and purified by an appropriate combination of known techniques. These methods include, for example: methods utilizing solubility such as salt precipitation and solvent precipitation; methods utilizing the difference in molecular weight, such as dialysis, ultrafiltration, gel-filtration, and SDS-polyacrylamide gel electrophoresis; methods utilizing a difference in electrical charge, such as ion-exchange column chromatography; methods utilizing specific affinity, such as affinity chromatography; methods utilizing a difference in hydrophobicity, such as reverse-phase high performance liquid chromatography; methods utilizing a difference in isoelectric point, such as isoelectric focusing electrophoresis; and, metal affinity columns, such as Ni-NTA. If an operatively linked purification tag, such as HA, is included in the fusion polypeptide, the purification tag can be utilized to purify the fusion polypeptide.

As noted herein, the fusion polypeptides of the presently-disclosed subject matter can also be prepared through chemical synthesis according to methods known in the art. Exemplary chemical synthesis methods of producing polypeptides include, but are not limited to: exclusive solid phase synthesis, partial solid phase methods, fragment condensation or classical solution synthesis. See, for example, Merrifield, J. Am. Chem. Soc. 85:2149, 1963; Stewart et al., Solid Phase Peptide Synthesis (2nd edition), Pierce Chemical Co., Rockford, Ill., 1984; Bayer and Rapp, Chem. Pept. Prot. 3:3, 1986; and Atherton et al., Solid Phase Peptide Synthesis: A Practical Approach, IRL Press, Oxford, 1989.

In some embodiments, a cell is provided that comprises a nucleotide sequence that encodes a fusion polypeptide comprised of a cell-penetrating polypeptide and a SNARE polypeptide aptamer in accordance with the presently-disclosed subject matter. Nucleic acids containing a target nucleotide sequence (e.g., a nucleotide sequence encoding a fusion polypeptide of the presently-disclosed subject matter) operably linked to a regulatory sequence can be introduced into a host cell transiently or, for long term regulation of gene expression, the nucleic acid can be stably integrated into the genome of the host cell or remain as a stable episome in the host cell.

As used herein, the term "host cell" is intended to include any cell or cell line, including prokaryotic and eukaryotic cells, into which a nucleic acid sequence of the presently-disclosed subject matter can be introduced and expressed. Exemplary host cells include, but are not limited to, yeast, fly, worm, plant, frog, and mammalian cells. Non-limiting examples of mammalian cell lines which can be used include CHO-cells (Urlaub and Chasm (1980) Proc. Natl. Acad. Sci. USA, 77:4216-4220), 293 cells (Graham et al. (1977) J Gen. Virol., 36:59) or myeloma cells like SP2 or NSO (Galfre and Milstein (1981) Meth. Enzymol., 73(B):3-46). Other exemplary eukaryotic host cells include insect (e.g., Sp. *frugiperda*), yeast (e.g., *S. cerevisiae, S. pombe, P. pastoris, K. lactis, H. polymorpha*; as generally reviewed by Fleer, R. (1992) Current Opinion in Biotechnology, 3(5):486496)), fungal and plant cells. Specific exemplary prokaryotic host cells include *E. coli* and *Bacillus* Sp.

Nucleic acids comprising a nucleotide sequence of the presently-disclosed subject matter operably linked to a regulatory sequence can be introduced into a host cell by standard techniques for transfecting cells. As used herein, the term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook, et al. (Molecular Cloning: A Laboratory Manual, 2nd Edition, Cold Spring Harbor Laboratory press (1989)), and other laboratory manuals.

Nucleotide sequences of the presently-disclosed subject matter operably linked to a regulatory sequence can be introduced into cells growing in culture by conventional transfection techniques (e.g., calcium phosphate precipitation, DEAE-dextran transfection, electroporation, etc.). In some embodiments, nucleotide sequences can also be transferred into cells in vivo, for example, by application of a delivery mechanism suitable for introduction of nucleic acid into cells in vivo into host production animals, such as retroviral vectors (see, e.g., Ferry, N. et al. (1991) Proc. Natl. Acad. Sci. USA, 88:8377-8381; and Kay, M. A. et al. (1992) Human Gene Therapy, 3:641-647), adenoviral vectors (see e.g., Rosenfeld, M. A. (1992) Cell, 68:143-155; and Herz, J. and Gerard, R D. (1993) Proc. Natl. Acad. Sci. USA, 90:2812-2816), receptor-mediated DNA uptake (see e.g., Wu, G. and Wu, C. H. (1988) J. Biol. Chem., 263:14621; Wilson et al. (1992) J Biol. Chem., 267:963-967; and U.S. Pat. No. 5,166,320), direct injection of DNA (see e.g., Acsadi et al. (1991) Nature, 332:815-818; and Wolff et al. (1990) Science, 247: 1465-1468) or particle bombardment (see e.g., Cheng, L. et al. (1993) Proc. Natl. Acad. Sci. USA, 90:4455-4459; and Zelenin, A. V. et al. (1993) FEBS Letters, 315:29-32).

Further provided, in some embodiments of the presently-disclosed subject matter, are methods for using the fusion polypeptides of the presently-disclosed subject matter (i.e., fusion polypeptides comprised of a cell-penetrating polypeptide and a SNARE polypeptide aptamer that is either a SNAP-23 amino terminus polypeptide fragment, such as the one provided in SEQ ID NO: 1, or a syntaxin 4 polypeptide fragment, such as the one provided in SEQ ID NO: 18). In some embodiments, methods for inhibiting neutrophil granule exocytosis are provided. In some embodiments, a method for inhibiting neutrophil exocytosis is provided that comprises contacting a neutrophil with an exemplary fusion polypeptide disclosed herein such that the fusion polypeptide enters the neutrophil and inhibits SNARE-associated neutrophil granule exocytosis.

As used herein, the terms "inhibit," "inhibition," or grammatical variations thereof refer to any decrease or suppression of SNARE-associated granule exocytosis in neutrophils, including, but not limited to, a decrease or suppression of secretory vesicle, specific granule, azurophil granule, and gelatinase granule exocytosis. It is understood that the degree of inhibition need not be absolute (i.e., the degree of inhibition need not be a complete prevention of SNARE-associated neutrophil granule exocytosis such that granules are not exocytosed from neutrophils at all) and that intermediate levels of inhibition of SNARE-associated neutrophil granule exocytosis are contemplated by the presently-disclosed subject matter. As such, in some embodiments, the inhibition of SNARE-associated neutrophil granule exocytosis can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%.

In some embodiments, the fusion polypeptide inhibits neutrophil granule exocytosis by inhibiting formation of a trans-SNARE complex, by inhibiting SNARE-dependent granule fusion, or both. As noted herein, the formation of a trans-SNARE complex performs an integral role in mediating neutrophil granule docking and fusion to a cell membrane. By contacting a neutrophil with a fusion polypeptide that includes a cell-penetrating polypeptide and a SNARE-peptide aptamer though, the inventors of the presently-disclosed subject matter have discovered that the fusion polypeptide enters the neutrophil and binds to a SNARE-interaction motif of an endogenous SNARE protein to thereby block the association of the various SNARE proteins. This blocking of the association of the various SNARE proteins inhibits the formation of a trans-SNARE complex and, consequently, SNARE-dependent granule fusion.

Four classes of granules have been found in neutrophils, including secretory vesicles, specific granules, azurophil granules and gelatinase granules, and the determination of whether exocytosis of each class of granules has been inhibited can be achieved by detecting protein markers specific for a particular granule subset on the plasma membrane of neutrophils and/or by measuring the release of the components within the granules themselves. For example, exocytosis of secretory vesicles, specific granules, and azurophil granules can be determined by measuring the plasma membrane expression of the protein markers CD35, CD66b, and CD63, respectively, by flow cytometry. As another example, exocytosis of gelatinase granules can be measured by determining the amount of gelatinase released using an enzyme-linked immunosorbent assay (ELISA). In some embodiments, the fusion polypeptide inhibits exocytosis of a secretory vesicle, a specific granule, or a gelatinase granule.

As will be recognized by those of ordinary skill in the art, in embodiments where contacting a cell with a fusion protein of the presently-disclosed subject matter inhibits neutrophil granule exocytosis, the optimum amount of a fusion polypeptide used to inhibit neutrophil granule exocytosis can vary depending on the particular granule subset being inhibited as well as desired degree of inhibition. In some embodiments, SNARE-associated neutrophil granule exocytosis is inhibited by contacting a neutrophil with a concentration of the fusion polypeptide of about 0.5 µg/ml, about 0.8 µg/ml, about 1.0 µg/ml, about 1.5 µg/ml, about 2.0 µg/ml, about 2.5 µg/ml, about 3.0 µg/ml, about 3.5 µg/ml, about 4.0 µg/ml, about 4.5 µg/ml, about 5.0 µg/ml, about 5.5 µg/ml, about 6.0 µg/ml, about 6.5 µg/ml, about 7.0 µg/ml, about 7.5 µg/ml, about 8.0 µg/ml, about 8.5 µg/ml, about 9.0 µg/ml, about 9.5 µg/ml, or about 10.0 µg/ml. In some embodiments, a neutrophil is contacted with a concentration of the fusion polypeptide of above about 0.5 µg/ml. In some embodiments, the concentration of the fusion polypeptide is about 0.8 µg/ml. Of course, determination and adjustment of the amount of a fusion polypeptide to be used in a particular application, as well as when and how to make such adjustments, can be ascertained using only routine experimentation.

Still further provided, in some embodiments of the presently-disclosed subject matter, are methods for treating a neutrophil-mediated inflammatory disorder in a subject. In some embodiments, a method for treating a neutrophil-mediated inflammatory disorder in a subject is provided that comprises administering to the subject an effective amount of a fusion polypeptide disclosed herein such that the fusion polypeptide inhibits SNARE-associated exocytosis in neutrophils to thereby treat the inflammatory disorder.

As used herein, the terms "treatment" or "treating" relate to any treatment of neutrophil-mediated inflammatory disorder, including but not limited to prophylactic treatment and therapeutic treatment. As such, the terms "treatment" or "treating" include, but are not limited to: preventing a neutrophil-mediated inflammatory disorder or the development of a neutrophil-mediated inflammatory disorder; inhibiting the progression of a neutrophil-mediated inflammatory disorder; arresting or preventing the development of a neutrophil-mediated inflammatory disorder; reducing the severity of a neutrophil-mediated inflammatory disorder; ameliorating or relieving symptoms associated with a neutrophil-mediated inflammatory disorder; and causing a regression of the neutrophil-mediated inflammatory disorder or one or more of the symptoms associated with the neutrophil-mediated inflammatory disorder.

The phrase "neutrophil-mediated inflammatory disorder" is used herein to refer to inflammatory diseases or disorders which are caused, at least in part, or exacerbated by a neutrophil-mediated inflammatory response. Neutrophil-mediated inflammatory disorders are typically characterized by the accumulation of a large number of neutrophils in injured and/or inflamed tissues. As noted herein, neutrophils are normally found circulating in the blood and are poorly responsive to external stimuli. However, during inflammation, neutrophils are one of the first immune cells to migrate to the site of inflammation where they engage in a number of biological activities including, but not limited to, the release of cytokines, phagocytosis, the generation of reactive oxygen species, and degranulation. As such, neutrophil-mediated inflammatory responses have been implicated in a wide variety of inflammatory diseases or disorders. In some embodiments of the presently-disclosed methods for treating a neutrophil-mediated inflammatory disorder, the inflammatory disorder is selected from rheumatoid arthritis, acute gouty arthritis, acute glomerulonephritis, acute transplant rejection, traumatic brain and spinal cord injury, vasculitis, ischemia-reperfusion injury, acute lung injury associated with sepsis, or immune complex mediated lung injury.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) *Cancer Chemother Rep.* 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) *Cancer Chemother Rep.* 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Suitable methods for administering to a subject a fusion polypeptide in accordance with the methods of the presently-disclosed subject matter include, but are not limited to, systemic administration, parenteral administration (including intravascular, intramuscular, intraarterial administration), subcutaneous administration, and local injection. Where applicable, continuous infusion can enhance drug accumulation at a target site (see, e.g., U.S. Pat. No. 6,180,082).

The particular mode of drug administration used in accordance with the methods of the present subject matter depends on various factors, including, but not limited to, the vector and/or drug carrier employed, the severity of the condition to be treated, and mechanisms for metabolism or removal of the drug following administration. In some embodiments of the presently-disclosed methods for treating a neutrophil-mediated inflammatory disorder, an effective amount of the fusion polypeptide is administered to a subject by intravenous injection.

The term "effective amount" is used herein to refer to an amount of the therapeutic composition (e.g., a fusion polypeptide disclosed herein) sufficient to produce a measurable biological response (e.g., an inhibition of SNARE-associated exocytosis in neutrophils). Actual dosage levels of active ingredients in a therapeutic composition of the presently disclosed subject matter can be varied so as to administer an amount of the fusion polypeptide(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

A fusion polypeptide as described herein can comprise a therapeutic composition that includes a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The therapeutic compositions used in the methods can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

For additional guidance regarding formulation and dose, see U.S. Pat. Nos. 5,326,902 and 5,234,933; PCT International Publication No. WO 93/25521; Berkow, et al., (1997) *The Merck Manual of Medical Information*, Home ed. Merck Research Laboratories, Whitehouse Station, New Jersey; Goodman, et al., (2006) *Goodman & Gilman's the Pharmacological Basis of Therapeutics*, 11th ed. McGraw-Hill Health Professions Division, New York; Ebadi. (1998) *CRC Desk Reference of Clinical Pharmacology*. CRC Press, Boca Raton, Fla.; Katzung, (2007) *Basic & Clinical Pharmacology*, 10th ed. Lange Medical Books/McGraw-Hill Medical Pub. Division, New York; Remington, et al., (1990) *Remington's Pharmaceutical Sciences*, 18th ed. Mack Pub. Co., Easton, Pa.; Speight, et al., (1997) *Avery's Drug Treatment: A Guide to the Properties, Choice, Therapeutic Use and Economic Value of Drugs in Disease Management*, 4th ed. Adis International, Auckland/Philadelphia; and Duch, et al., (1998) *Toxicol. Lett.* 100-101:255-263.

The presently-disclosed subject matter is further illustrated by the following specific but non-limiting examples. Some of the following examples may include compilations of data that are representative of data gathered at various times during the course of development and experimentation related to the present invention.

EXAMPLES

Example 1

Production of Fusion Polypeptides

To generate the fusion polypeptides, total RNA from human neutrophils was first isolated using an RNeasy Mini kit (Qiagen, Valencia, Calif.). Reverse transcriptase-polymerase chain reaction (RT-PCR) primers were then designed according to the cDNA sequence of human SNAP-23 and syntaxins 4 and 6, depicted in FIGS. 1 and 2, respectively. All of the forward primer sets incorporated a NcoI restriction enzyme site and the reverse primer sets incorporated a HindIII restriction enzyme site. RT-PCR was then performed using the SuperScript™ One-Step RT-PCR kit (Invitrogen Life Technologies, Carlsbad, Calif.) under the following conditions: 30 min at 50° C. for cDNA synthesis, 2 min at 94° C. for strand denaturation, followed by 40 cycles of 30 sec steps at 94° C. (denaturation), 55° C. (annealing), and 68° C. (extension), and the final extension step of 72° C. for 10 min. The PCR product was then digested with NcoI and HindIII (Promega, Madison, Wis.) and ligated into a pTAT-HA plasmid using T4 DNA ligase (Promega, Madison, Wis.). Plasmids were propagated in DH5α chemically-competent *Escherichia coli* cells (Invitrogen Life Technologies, Carlsbad, Calif.). Cloning was confirmed by DNA sequencing.

Expression of the plasmids was then conducted in BL21 (DE3) pLysS chemically competent *E. coli* cells. Purification of the TAT fusion proteins was performed by sonication of the bacterial pellet, followed by protein separation from the supernatant by Ni-NTA column chromatography, after which protein was eluted using a pH gradient combined with washing with 60% isopropanol to remove LPS. Protein concentration was measured by DC protein assay (Bio-Rad Laboratories, Hercules, Calif.). TAT-SNARE peptides were then further confirmed by coomassie blue staining, and by immunoblot using anti-HA-tag, anti-His-tag, and antibodies for SNAP-23 (amino and carboxyl terminus), syntaxin 4 and 6.

Figure 2:
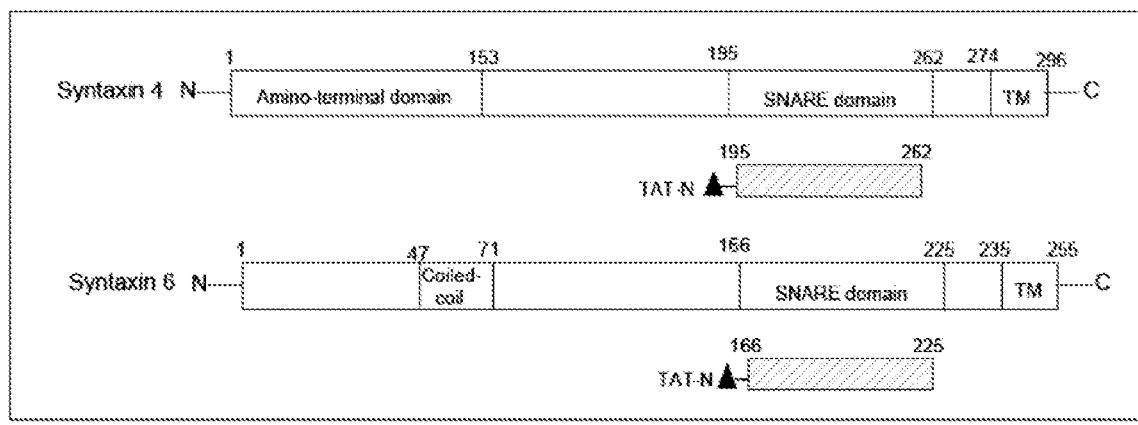
FIG. 2 is a schematic diagram of exemplary syntaxin 4 and syntaxin 6 polypeptides expressed as TAT fusion polypeptides, where the triangle and stick represent the TAT sequence and the hemagglutinin tag, and where the upper numbers correspond to the amino acid positions.
Figure 3:
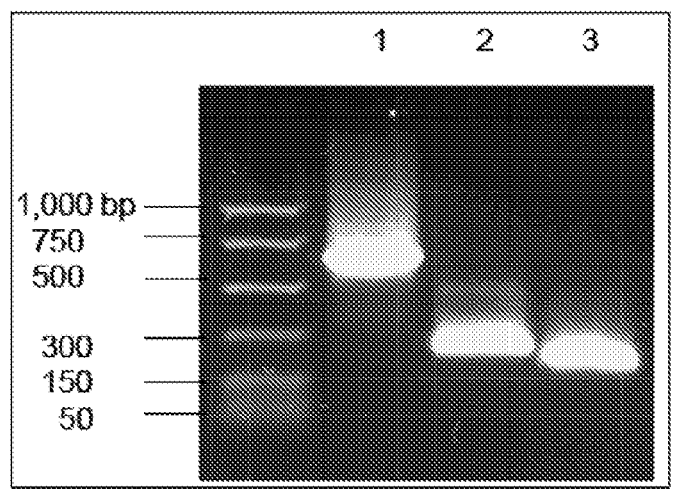
FIG. 3 is a photograph of an agarose gel showing SNAP-23 nucleic acid sequences that were obtained by reverse transcriptase-polymerase chain reaction (RT-PCR) amplification of total RNA from human neutrophils. Lane 1 represents the full length SNAP-23 (690 bp), Lane 2 represents a PCR fragment corresponding to the amino-terminus of SNAP-23 (272 bp), and Lane 3 represents a PCR fragment corresponding to the carboxyl terminus of SNAP-23 (228 bp).

With particular regard to the generation of a SNAP-23 fusion polypeptide, it was first noted that SNAP-23a contains two coiled-coil motifs (residues 1-78 and 144-208), as shown in FIG. 1. Based on this information, three sets of primers, incorporating an NcoI restriction site on the forward primer and a HindIII restriction site on the reverse primer, were designed to generate the amino-terminus, the carboxyl-terminus, and the whole SNAP-23 cDNA sequence. Primer set 1 was designed to generate the whole SNAP-23 protein with the forward primer incorporating a NcoI restriction enzyme site 5'CTTGAGTTTTGATTCACCATGGATAAT3' (SEQ ID NO: 14), and the reverse primer incorporating a HindIII restriction enzyme site 5'GAAGTGAATAAGCTTTAAA-GAAGAACA3' (SEQ ID NO: 15). Primer set 2 was designed to generate the amino-terminus of SNAP-23 with the forward primer the same as in primer set 1 and the reverse primer incorporating a HindIII restriction enzyme site 5'CAGACA-CAAAGCTTACATCATTTGTTGA3' (SEQ ID NO: 16). Primer set 3 was designed to generate the carboxyl-terminus of SNAP-23 with the forward primer incorporating a NcoI restriction enzyme site 5'AGAGAAGATGCCATGGAA-GAGAAC3' (SEQ ID NO: 17), and the reverse primer the same as in primer set 1. Total RNA isolated from unstimulated neutrophils was then subjected to RT-PCR to generate SNAP-23 cDNA and SNARE motif fragments. FIG. 3 shows the different cDNA fragments amplified by RT-PCR. Primer set 1 generated the full length SNAP-23 with an expected product of 690 bp, primer set 2 generated an amino-terminus fragment with an expected size of 272 bp, and primer set 3 generated a carboxyl-terminus fragment of 228 bp. Verification of each PCR product generated for each segment of SNAP-23 (FIG. 3) was accomplished by DNA sequencing.

Figure 4:
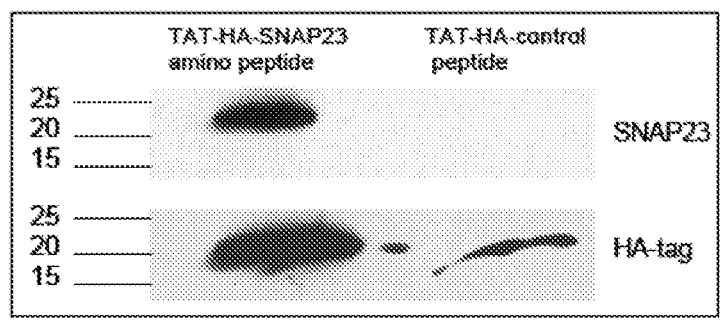
FIG. 4 is a photograph of a western blot confirming the expression of a TAT-hemagglutinin(HA)-SNAP-23 fusion polypeptide in bacterial cells.

The PCR product of the amino-terminus of SNAP-23 and the pTAT-HA vector were then digested with NcoI and HindIII, ligated, and used for the transformation of *Escherichia coli* DH5 competent cells. Colonies were selected and DNA sequencing confirmed the PCR product contained the amino-terminus portion of SNAP-23. Transformed *E. coli* BL21 cells were used as a host to overexpress the recombinant TAT fusion protein. The fusion polypeptide, comprised of a TAT cell-penetrating polypeptide, a hemagglutinin affinity tag, and 78 amino acids (SEQ ID NO: 1) from the amino-terminus of SNAP-23 (referred to hereinafter as "TAT-HA-SNAP-23" or "TAT-SNAP-23"; SEQ ID NO: 12), was then confirmed by Western blotting (FIG. 4). Briefly, equal amounts of TAT-HA-SNAP-23 and a TAT-HA control peptide were analyzed by SDS-PAGE and immunoblotted with an antibody that recognizes the SNAP-23 amino-terminus region. The blots were then stripped and re-probed with an HA antibody. FIG. 4 shows the immunoblot for fusion proteins containing the amino terminal SNAP-23 SNARE domain (TAT-HA-SNAP-23) and the vector alone (TAT-HA-control peptide).

Example 2

Introduction of Fusion Polypeptides into Neutrophils

In order to introduce the fusion polypeptides in neutrophils, blood was first obtained from healthy donors in accordance with a protocol approved by the University of Louisville, Human Studies Committee. Neutrophils were then isolated from healthy volunteers using plasma-Percoll gradients as described previously (34). Trypan blue staining showed previously that greater than 97% of cells obtained by that method were neutrophils with greater than 95% viability. After isolation, neutrophils were then suspended in Krebs-Ringer phosphate buffer (KRPB; pH 7.2) at the desired concentration.

Figure 5:
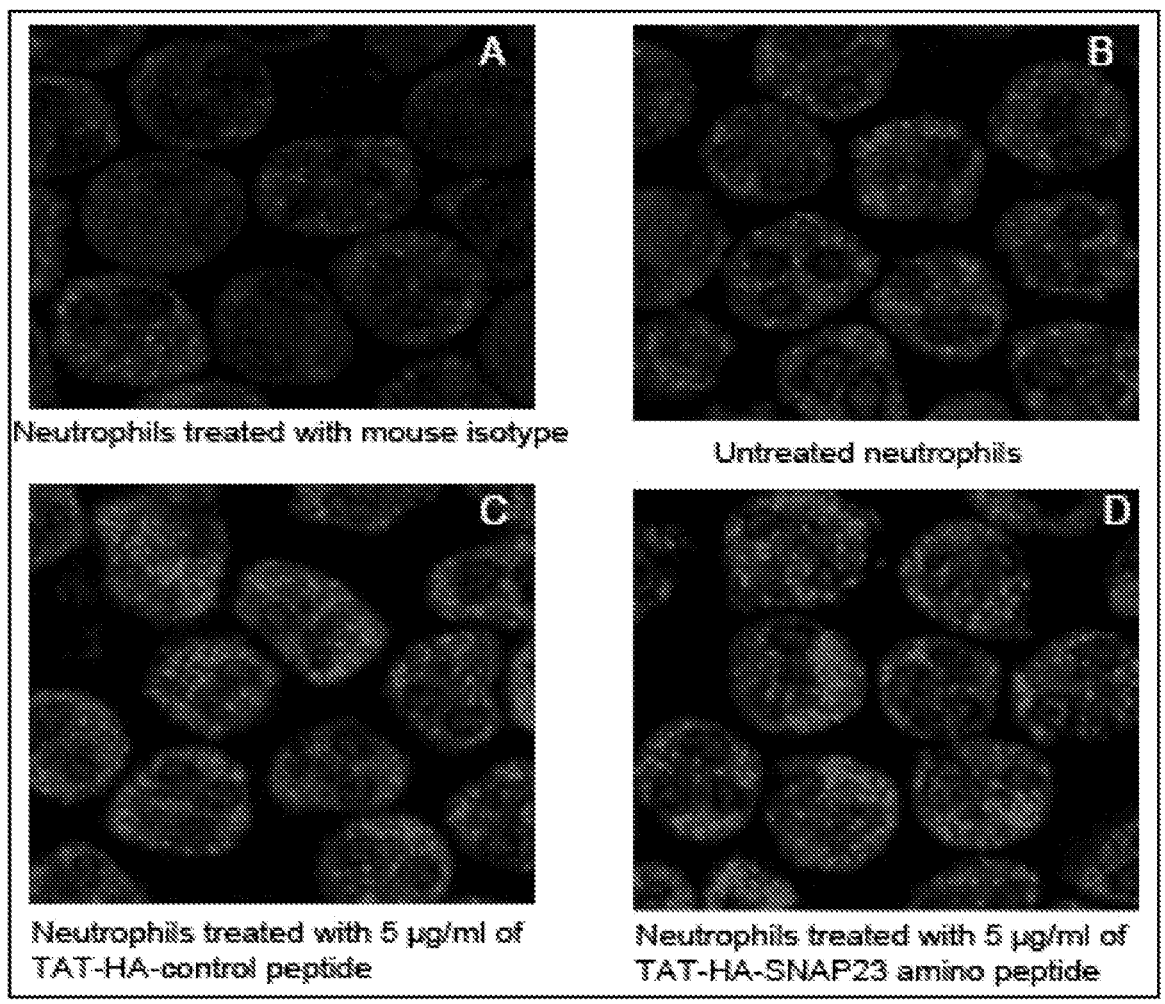
FIG. 5 includes confocal microscopy images of human neutrophils treated with a mouse isotype (FIG. 5A), untreated (FIG. 5B), treated with 5 µg/ml of a TAT-HA control peptide after a 30 min incubation at 37° C.

To examine transduction of TAT-fusion polypeptides, human neutrophils were incubated with the fusion proteins for 10 min at 37° C., then the cells were fixed, immunostained with HA antibody, and examined by confocal microscopy using a Zeiss LSM 510 confocal microscope, as previously described (20, 21). To visualize TAT-fusion polypeptide uptake, each polypeptide was labeled with fluorescein (NHS-Fluorescein, Pierce, Rockford, Ill.) according to the manufacturer's instructions. TAT-fusion proteins (TAT-HA-control peptides and TAT-HA-SNAP-23 polypeptides) showed a punctate cytosolic distribution (FIG. 5), as described for other TAT-fusion proteins [23,28]. Incubation of neutrophils with 5 µg/ml of the fusion polypeptides for 30 min at 37° C. showed that approximately 80% of neutrophils demonstrated TAT-fusion protein transduction. Trypan blue quenching demonstrated FITC-conjugated fusion proteins were internalized.

Example 3

Effect of Fusion Polypeptides on Neutrophil Viability

To evaluate whether the introduction of a TAT-fusion protein affected neutrophil survival, neutrophils were treated for 30 min at 37° C. with increasing concentrations of the TAT-HA-SNAP-23 polypeptide (1-40 µg/ml) and cell viability was measured by Trypan Blue dye exclusion. As shown in Table 2 below, the TAT-SNAP-23 fusion protein had no significant effect on neutrophil survival.

TABLE 2

Cell viability of neutrophils exposed to TAT-HA-SNAP-23 fusion polypeptide.

| | TAT-HA-SNAP-23 amino peptide (µg/ml) | | | | | | |
|---|---|---|---|---|---|---|---|
| | 0(UT) | 1 | 3 | 5 | 10 | 20 | 40 |
| Cell Viability (% UT) | 100 | 89 | 97.6 | 78.5 | 88.2 | 76.0 | 78.0 |

Example 4

Inhibition of Neutrophil Exocytosis by Fusion Polypeptides

Exocytosis can be measured for each neutrophil granule subset by the expression of CD35, CD66b, and CD63, and by the release of gelatinase. CD35, CD66b and CD63 are specific membrane markers of secretory vesicles, specific granules and azurophil granules, respectively. Expression of CD35 (secretory vesicles), CD66b (specific granules), and CD63 (azurophil granules) was determined by flow cytometry, as previously described (5, 22). Gelatinase (MMP-9) was measured in the supernatants of $4 \times 10^6$ neutrophils/ml, using an ELISA kit according to the manufacture's instructions (R & D Systems, Minneapolis, Minn.).

Figure 6:
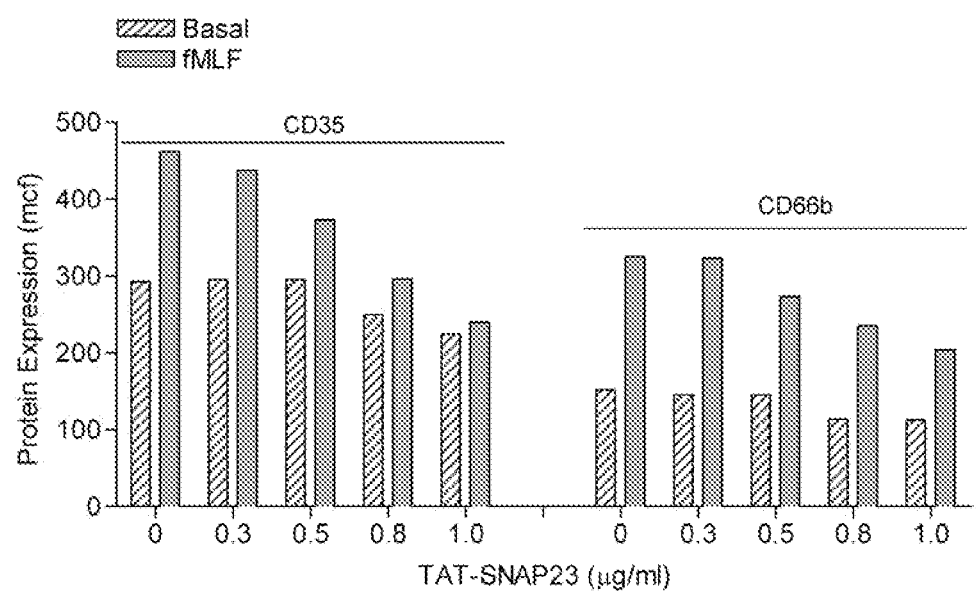
FIG. 6 is a dose response curve showing the effect of various concentrations of an exemplary TAT-HA-SNAP-23 fusion polypeptide on secretory vesicle (CD35) and specific granule (CD66b) exocytosis, where the various concentrations of the TAT-HA-SNAP-23 fusion polypeptide (x-axis) are plotted against the mean channel fluorescence (mcf) intensity of CD35 and CD66b (y-axis).

A dose response curve was initially performed with TAT-SNAP-23 polypeptides using concentrations of the polypeptides from 0.3 to 1.0 µg/ml. Neutrophils were incubated with varying concentrations of the TAT-SNAP-23 polypeptide for 30 min at 37° C. prior to measuring exocytosis of secretory vesicles (CD35 expression) and specific granules (CD66b) by flow cytometry. As shown in FIG. 6, the TAT-SNAP-23 fusion peptide inhibited N-formyl-methionyl-leucyl-phenylalanine (fMLP)-stimulated exocytosis of secretory vesicles and specific granules in a dose dependent manner.

Figure 7:
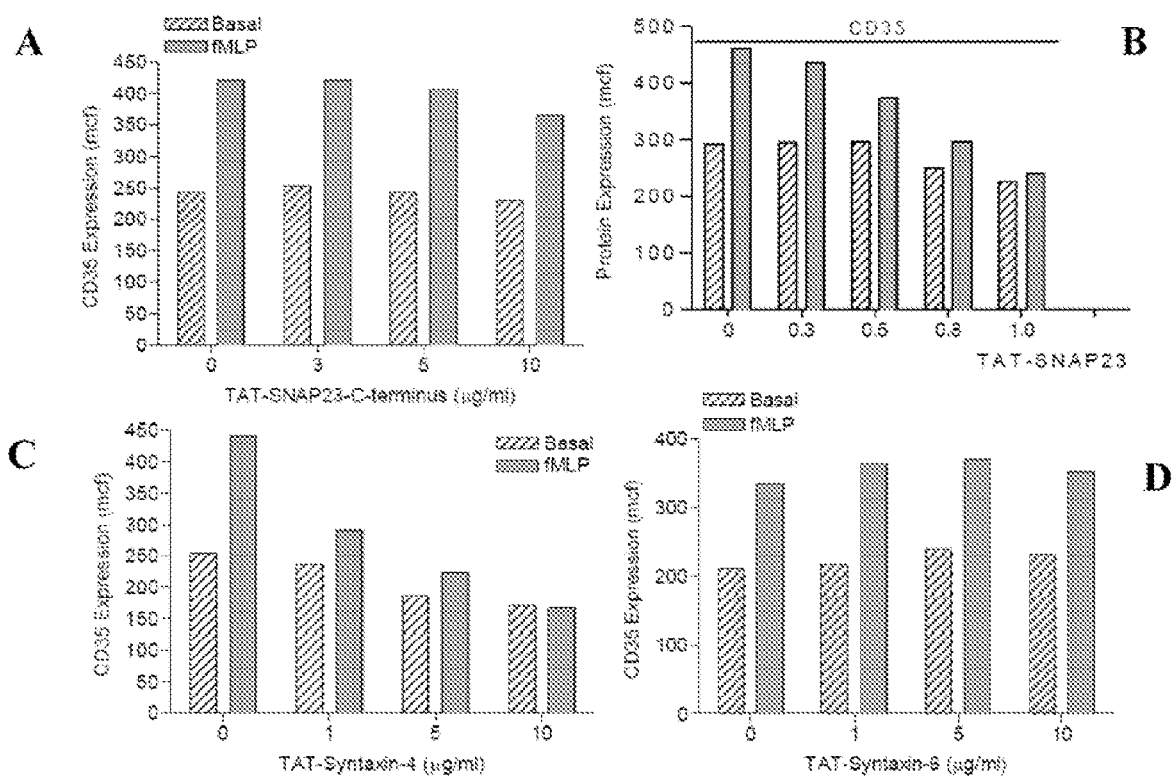
FIG. 7 includes graphs showing the effect of various fusion polypeptides on formyl-methionyl-leucyl phenylalanine (fMLF)-stimulated exocytosis of secretory vesicles in human neutrophils, where the neutrophils were contacted with either a TAT fusion polypeptide containing a carboxy-terminus of SNAP-23 (FIG. 7A; TAT-SNAP-23-C-terminus), an amino terminal SNARE domain of SNAP-23 (FIG. 7B; TAT-SNAP-23), the SNARE domain of syntaxin 4 (FIG. 7C; TAT-Syntaxin-4), or syntaxin 6 (FIG. 7D; TAT-Syntaxin-6).

A concentration-inhibition curve for fMLF-stimulated exocytosis of secretory vesicles (CD35) was then generated for each of the TAT fusion proteins. FIG. 7 shows that the TAT-fusion proteins containing the amino terminal SNARE domain (SEQ ID NO: 1) of SNAP-23 (TAT-SNAP-23) and the SNARE domain of syntaxin 4 (SEQ ID NO: 18) inhibited fMLF-stimulated exocytosis (FIGS. 7B and 7C, respectively), while those containing the carboxy terminus of SNAP-23 (SEQ ID NO: 3) or syntaxin-6 had no effect (FIGS. 7A and 7D, respectively). Similar experiments were further performed with fusion polypeptides that included either a 40 amino acid fragment (SEQ ID NO: 2) from the amino-terminal SNARE domain of SNAP-23 or a 24 amino acid fragment (SEQ ID NO: 4) from the carboxy-terminus of SNAP-23, but neither of those shorter fragments inhibited exocytosis at the concentrations tested.

Figure 8:
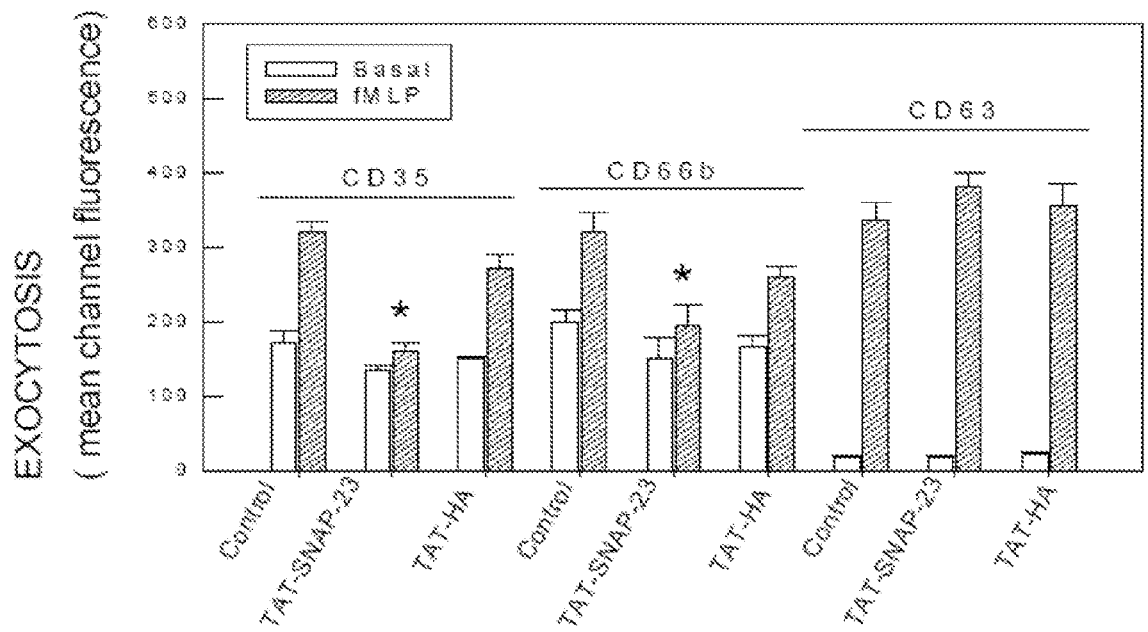
FIG. 8 is a graph depicting the inhibition of secretory vesicle (CD35), specific granule (CD66b), and azurophil granule (CD63) exocytosis in human neutrophils contacted with 0.8 µg/ml of a fusion polypeptide comprised of a TAT polypeptide and the amino terminal SNARE domain of SNAP-23 (TAT-SNAP-23) or a TAT-hemagglutinin fusion polypeptide (TAT-HA) as a control.
Figure 9:
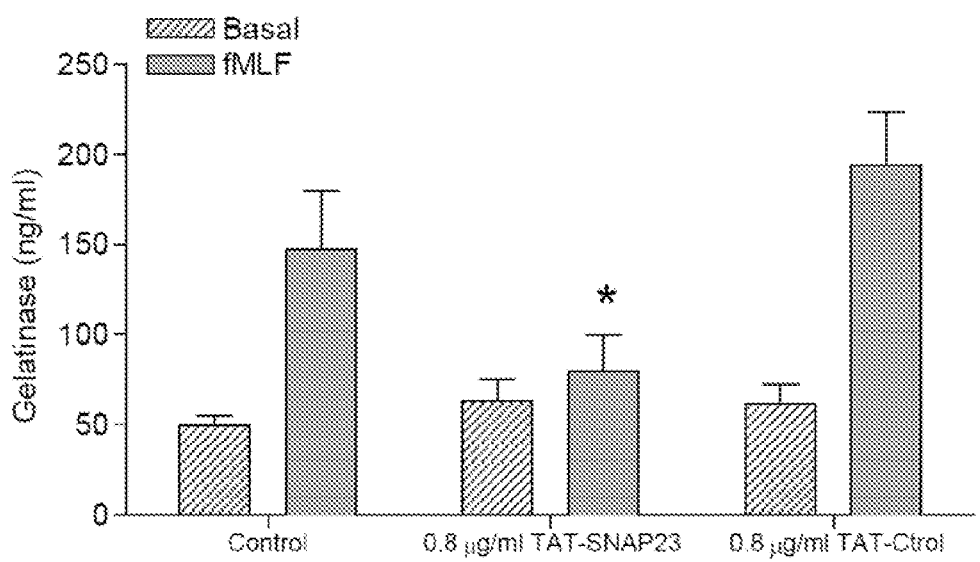
FIG. 9 is a graph showing the results of an ELISA experiment used to measure gelatinase in basal and fMLF-stimulated human neutrophils contacted with either 0.8 µg/ml of a fusion polypeptide comprised of a TAT polypeptide and the amino terminal SNARE domain of SNAP-23 (TAT-SNAP-23), or a TAT-hemagglutinin (TAT-HA) control polypeptide.

To determine the efficiency of TAT-SNAP-23 on inhibition of all four neutrophil granule subsets, the ability of 0.8 µg/ml TAT-SNAP-23 or TAT-Control to inhibit fMLF-stimulated exocytosis was then compared. FIG. 8 shows that TAT-SNAP-23 inhibited secretory vesicle (CD35) exocytosis by 90% and specific granule (CD66b) exocytosis by 75%, while the TAT-Control had no effect. On the other hand, neither the TAT-Control nor the TAT-SNAP-23 polypeptide altered exocytosis of azurophil granules (CD63) stimulated by fMLP in the presence of latrunculin A. Similar levels of inhibition were also seen for secretory vesicle and specific granule exocytosis stimulated by platelet-activating factor (PAF) and TNFα (see FIG. 18). As noted above, the ability of the TAT-fusion proteins to inhibit fMLP-stimulated exocytosis of gelatinase granules was also measured by release of gelatinase by ELISA. FIG. 9 shows that TAT-SNAP-23 also significantly reduced fMLP-stimulated gelatinase release by 90%, while the TAT-HA control protein had no effect.

Previous studies showing that SNAP-23 does not participate in azurophil granule exocytosis in human neutrophils explains the finding that TAT-SNAP-23 did not inhibit exocytosis of that granule subset. However, previous studies (13) have reported that a polyclonal antibody against syntaxin 6 inhibited both specific and azurophilic granules. Further, others (14) have reported that introduction of an anti-syntaxin 4 antibody into electropermeabilized neutrophils blocked CD66b up-regulation, indicating that syntaxin 4 can be involved in exocytosis of specific granules. Based on these reports, TAT-fusion peptides for other SNARE proteins, including syntaxin 4 and 6 and VAMP1, 2, and 7, can be created and it is predicted that these fusion proteins can prevent exocytosis of different combinations of granule subsets.

Figure 10:
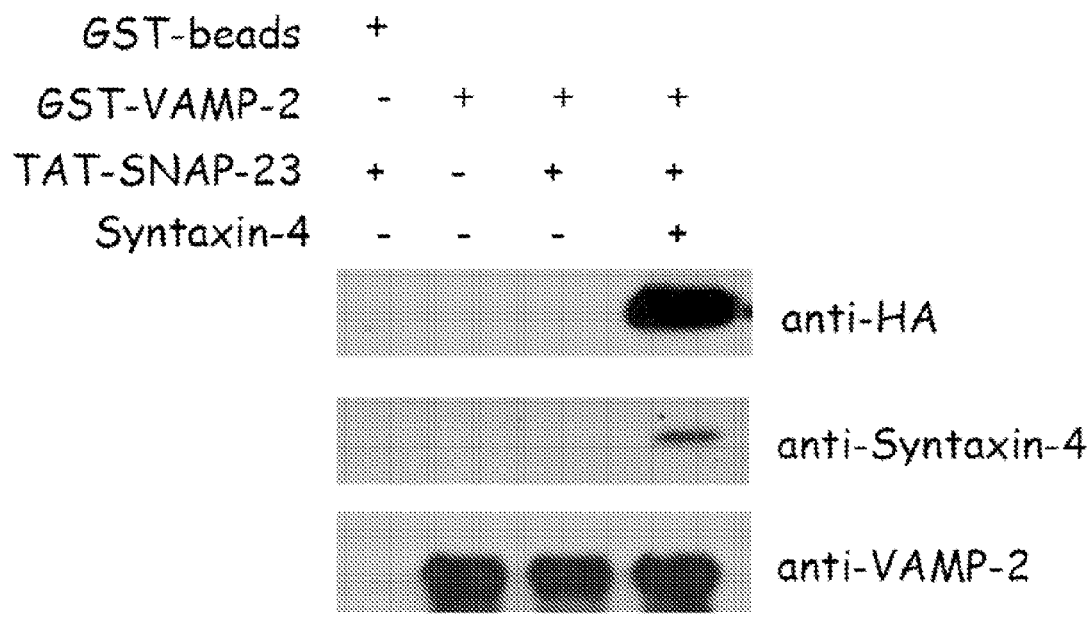
FIG. 10 includes images of an immunoblot analysis of a glutathione S-transferase (GST) pull down experiment where GST-VAMP-2 was incubated with or without syntaxin-4 and a fusion polypeptide comprised of a TAT polypeptide and the amino terminal SNARE domain of SNAP-23 (TAT-SNAP-23).

Further to the specific granule inhibition studies described herein above, it was thought that TAT-fusion proteins containing SNARE domains inhibited exocytosis by binding to endogenous SNARE proteins, preventing their interaction which is required for fusion of two membrane bound compartments. To determine if this is the mechanism by which TAT-SNAP-23 acts, the ability of TAT-SNAP-23 to bind to recombinant SNARE proteins in vitro was examined VAMP-2 was first generated as a GST fusion protein, and bound to glutathione beads. The ability of TAT-SNAP-23 to bind to VAMP-2 alone and to VAMP-2 complexed with syntaxin-4 was then examined by a GST pull down experiment followed by immunoblotting for the HA tag on TAT-SNAP-23. FIG. 10 shows the result of this experiment demonstrating that TAT-SNAP-23 did not bind to GST beads or to GST-VAMP-2. However, TAT-SNAP-23 strongly bound to the complex of VAMP-2 and syntaxin-4 indicating that the TAT-SNAP-23 polypeptides were inhibiting exocytosis by binding to endogenous SNARE proteins or complexes of those proteins.

Figure 11:
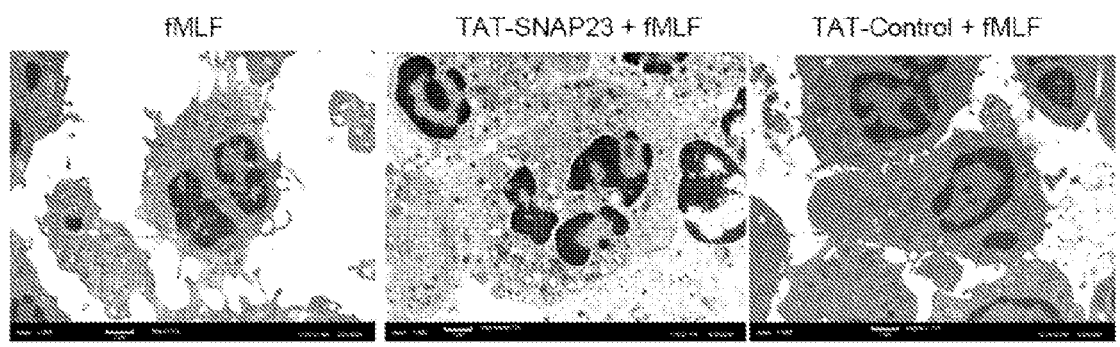
FIG. 11 includes transmission electron microscopy images of human neutrophils pre-treated with or without a fusion polypeptide comprised of a TAT polypeptide and the amino terminal SNARE domain of SNAP-23 (TAT-SNAP-23), or a TAT-control polypeptide, prior to stimulation with 300 nM fMLF for 2 min.

To further confirm that TAT-SNAP-23 polypeptides specifically inhibited exocytosis of neutrophil granules, transmission electron microscopy of human neutrophils pre-treated with or without TAT-SNAP-23 or TAT-Control prior to stimulation with 300 nM fMLF for 2 min was performed. FIG. 11 shows that the number of granules inside the neutrophils was significantly reduced in untreated cells or cells pre-treated with TAT-Control. On the other hand, pre-treatment with TAT-SNAP-23 resulted in neutrophils that retained most of their granules. These results thus indicate that TAT-SNAP-23 impairs neutrophil degranulation.

Figure 12:
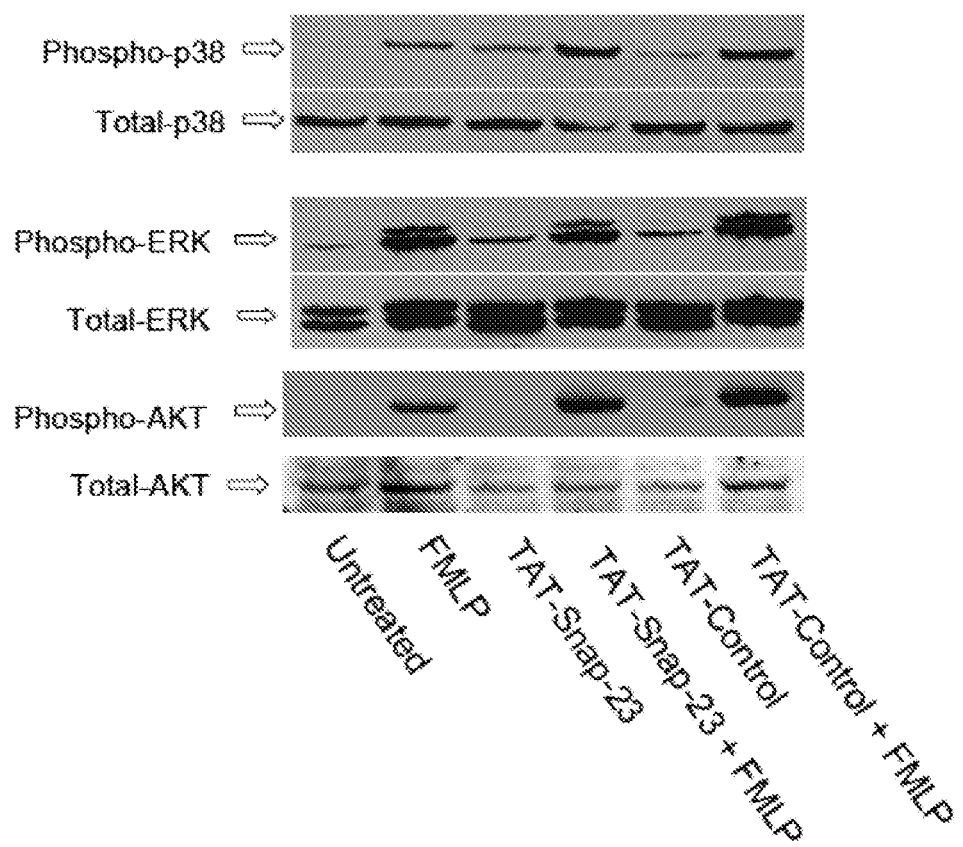
FIG. 12 includes photographs showing the results of an immunoblot analysis for total and phosphorylated p38 MAPK, ERK1/2, and Akt in lysates of neutrophils pre-treated with or without a TAT-control polypeptide and a fusion polypeptide comprised of a TAT polypeptide and the amino terminal SNARE domain of SNAP-23 (TAT-SNAP-23), and then stimulated for 2 min with or without 300 nM fMLP.

To determine if TAT-SNAP-23 alters neutrophil exocytosis by mechanisms other than impaired SNARE protein interaction or that it has other, non-specific effects on neutrophil function, the effect of pre-treatment with or without TAT-SNAP-23 and TAT-Control on fMLF-stimulated signal transduction pathways was also examined. Activation of ERK, p38 MAPK, and Akt were determined by immunoblot analysis for phosphorylated (i.e., activated) forms of these kinases. FIG. 12 shows that neither TAT-fusion protein altered basal or stimulated activation of any of these kinases.

Example 5

Effect of Fusion Polypeptides on In Vivo Neutrophil-Mediated Lung Injury

To determine the effect of the TAT-SNAP-23 fusion polypeptide on neutrophil-mediated lung injury in vivo, the ability of the TAT-SNAP-23 polypeptides to enter rat neutrophils was first established. Briefly, neutrophils were obtained from rats by peritoneal lavage 4 hr after intraperitoneal administration of thioglycolate. These neutrophils were incubated with 5 µg/ml TAT-SNAP-23 for 10 min, fixed, and stained with fluorescent-labeled anti-HA antibody. Confocal microscopy demonstrated punctate fluorescence staining of 75% to 80% of cells, similar to that shown in FIG. 5 for human neutrophils.

To determine if TAT-SNAP-23 entered rat neutrophils in vivo, 20 µg of TAT-SNAP-23 was injected into a subcutaneous air pouch 2 hr after injection of carrageenan to induce inflammation. Cells were obtained by lavage of the air pouch, stained with anti-HA, and examined by confocal microscopy. Approximately 50% of neutrophils demonstrated fluorescence staining To further determine if TAT-SNAP-23 or TAT-Control polypeptides were toxic when administered systemically to rats, each was injected intravenously at 0.5 mg/kg and the rats were observed for 24 hrs. No obvious distress was noted and the rats survived without problems.

Figure 13:
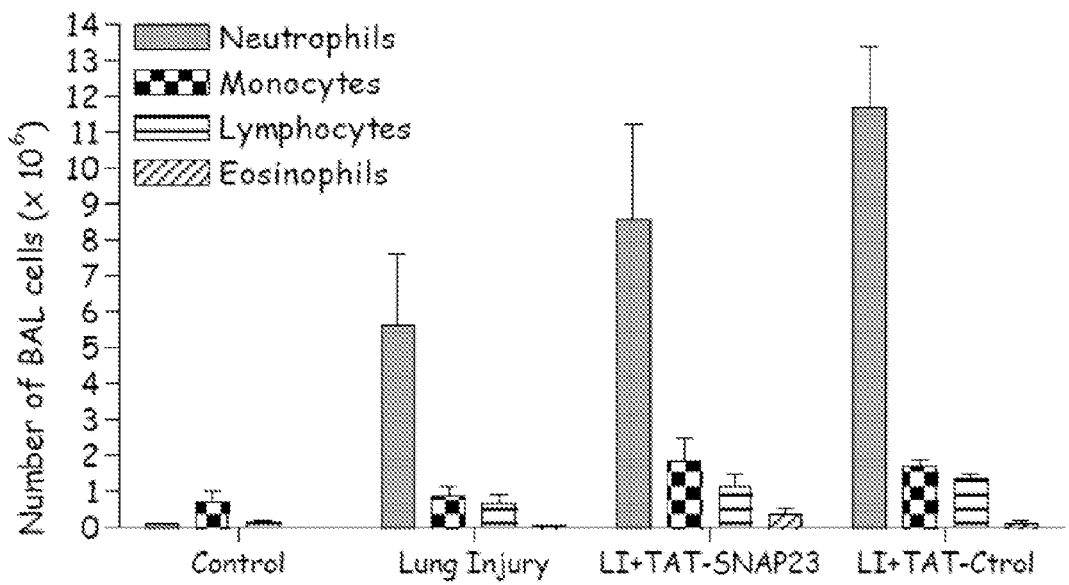
FIG. 13 is a graph depicting the number of neutrophils, monocytes, lymphocytes, and eosinophils present in bronchoalveolar lavage (BAL) fluid obtained from rats with immune-complex mediated lung injury that were treated with or without a TAT-Control polypeptide or a fusion polypeptide comprised of a TAT polypeptide and the amino terminal SNARE domain of SNAP-23 (TAT-SNAP-23) two hours after initiation of immune complex deposition.
Figure 14:
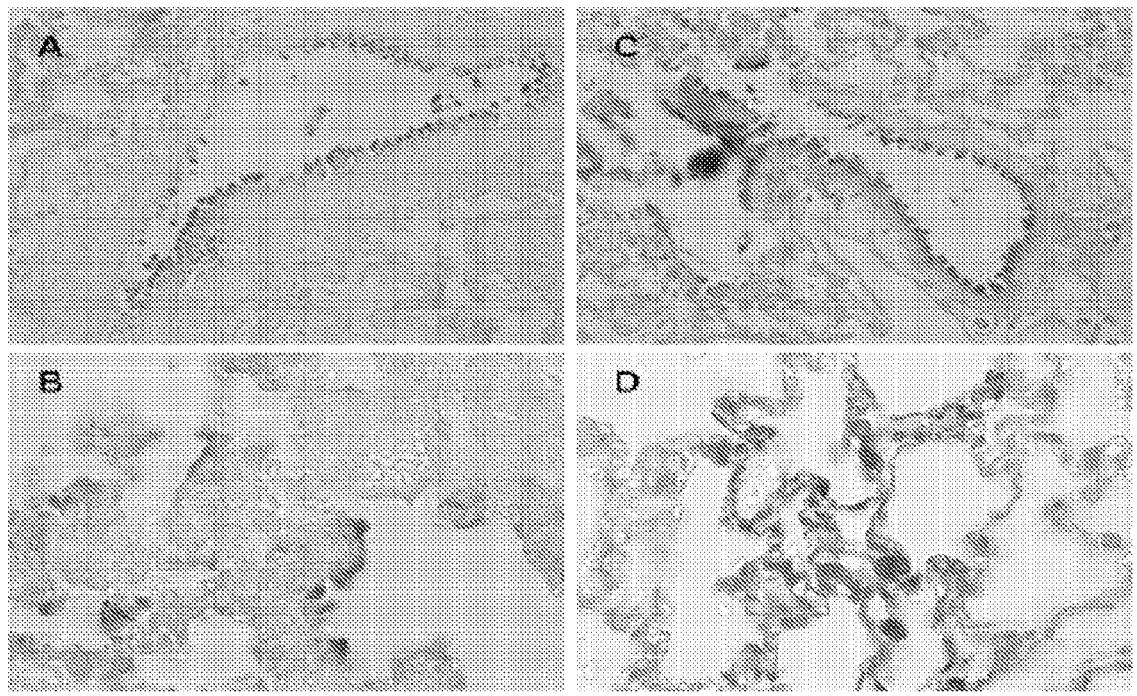
FIG. 14 includes immunohistochemistry images of lung sections immunostained for myeloperoxidase and taken from rats following immune complex lung injury without (FIGS. 14A and 14B) and with (FIGS. 14C and 14D) administration of 0.05 mg/kg of a fusion polypeptide comprised of a TAT polypeptide and the amino terminal SNARE domain of SNAP-23 (TAT-SNAP-23) two hours after immune complex depositions.
Figure 15:
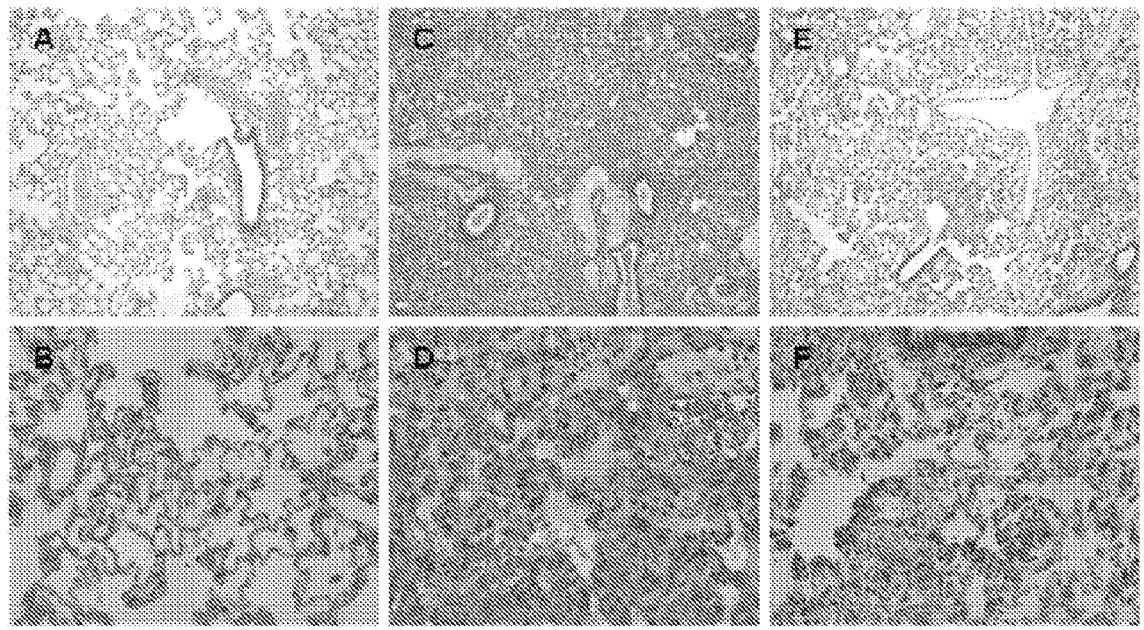
FIG. 15 includes images of hematoxylin and eosin stained lung sections from normal rats (FIGS. 15A and 15B), from rats 4 hrs after immune complex deposition (FIGS. 15C and 15D), and from rats that received 0.5 mg/kg of a fusion polypeptide comprised of a TAT polypeptide and the amino terminal SNARE domain of SNAP-23 (TAT-SNAP-23) two hours prior to sacrifice (FIGS. 15E and 15F).
Figure 16:
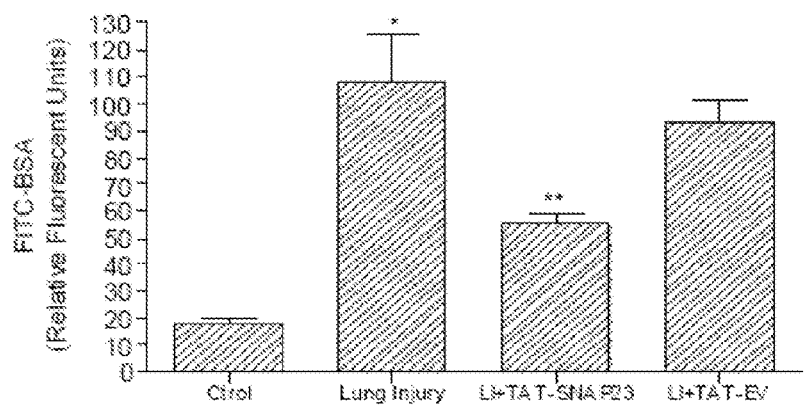
FIG. 16 is a graph depicting the extent of vascular leakage in rats receiving intratracheal administration of phosphate-buffered saline (Ctrol) or 0.18 mg of anti-bovine serum albumin (BSA) antibodies (Lung Injury or "LI") followed by intravenous administration of 10 mg of BSA trace-labeled with 250 μg of FITC-BSA. Groups receiving a fusion polypeptide comprised of a TAT polypeptide and the amino terminal SNARE domain of SNAP-23 (TAT-SNAP-23) or a TAT-Control polypeptide, 0.5 mg/kg each, were injected with the respective polypeptides two hours prior to sacrifice.

Further to the studies described herein above, lung injury was induced in pathogen-free male Long-Evans rats, as previously described (36-39), to determine whether the TAT-SNAP-23 polypeptides effectively inhibit neutrophil-mediated inflammation in vivo. Briefly, a rat model of immune complex-mediated lung injury induced by intravenous administration of bovine serum albumin (BSA) and intratracheal administration of anti-BSA antibodies was used to examine the ability of TAT-SNAP-23 and TAT-Control polypeptides to alter neutrophil accumulation in rat lungs and to inhibit lung injury. Intravenous injection of 0.05 mg/kg TAT-SNAP-23 or TAT-control 2 hours after initiation of injury had no effect on neutrophil accumulation in the lungs after immune complex-induced injury, as measured by an ELISA of lung tissue for myeloperoxidase (MPO) and cell count of bronchoalveolar lavage fluid (FIG. 13). Further, as determined by immunohistochemistry of lung sections for MPO, administration of 0.05 mg/kg had no effect on neutrophil adherence to bronchiolar epithelial cells (FIG. 14C) or migration into lung parenchyma (FIG. 14D) when compared with similar section from control rats (FIGS. 14A and B, respectively). However, hematoxylin and eosin staining of lung sections from normal rats (FIGS. 15A and 15B), from rats 4 hrs following immune complex deposition (FIGS. 15C and 15D), and following administration of 0.5 mg/kg TAT-SNAP-23 two hours prior to sacrifice (FIGS. 15E and 15F) demonstrated a marked reduction in lung edema and disruption of alveoli following administration of TAT-SNAP-23, compared to control animals. The degree of vascular injury in the lungs was evaluated by leakage of FITC-labeled albumin into the alveolar space, detected as fluorescence in bronchoalveolar lavage fluid. FIG. 16 shows that intravenous administration of TAT-SNAP-23 two hours after initiation of injury and two hours prior to sacrifice significantly reduced albumin leakage. Together, these studies thus indicate that administration of TAT-SNAP-23 after induction of immune complex injury inhibits neutrophil-mediated inflammation in vivo.

Example 6

Effect of Fusion Polypeptides on Neutrophil Functional Responses

Figure 17:
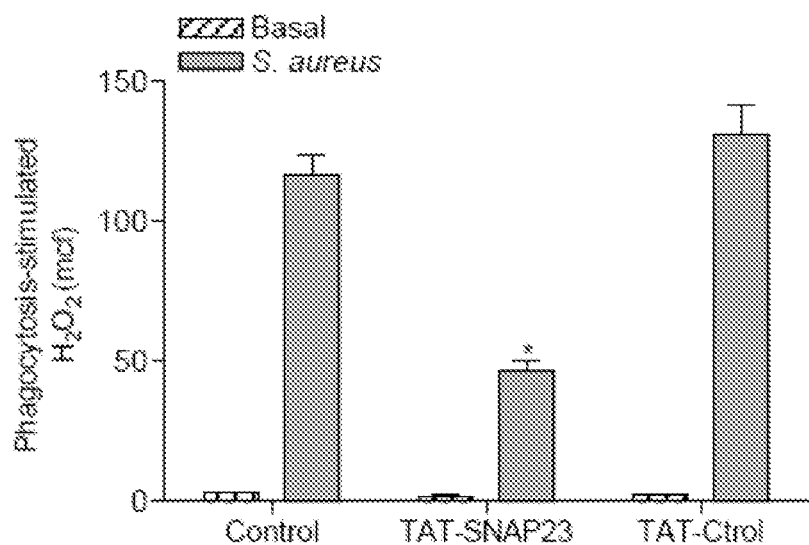
FIG. 17 is a graph showing the effect of a fusion polypeptide comprised of a TAT polypeptide and the amino terminal SNARE domain of SNAP-23 (TAT-SNAP-23) and a TAT-Control polypeptide on phagocytosis stimulated $H_2O_2$ production, where mean channel fluorescence (y-axis) is plotted against the various experimental groups (x-axis).

Given the ability of TAT-SNAP-23 fusion proteins to inhibit fMLF-stimulated exocytosis of secretory vesicles, gelatinase granules, and specific granules, the effect of 0.8 µg/ml TAT-SNAP-23 and TAT-Control on fMLF-stimulated superoxide release, phagocytosis-stimulated $H_2O_2$ production, and on PAF- and TNFα-induced priming of these activities was examined. TAT-SNAP-23 had no effect on bacterial phagocytosis, however, phagocytosis-stimulated $H_2O_2$ production was significantly reduced by approximately 50% (FIG. 17).

Figure 18:
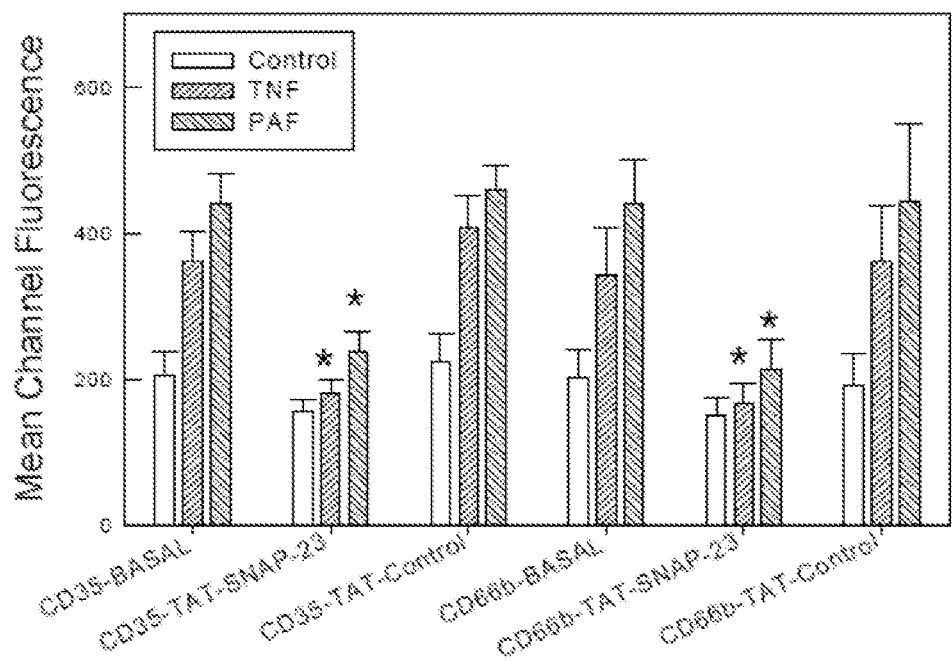
FIG. 18 is a graph depicting the inhibition of secretory vesicle (CD35) and specific granule (CD66b) exocytosis in TNFα and PAF primed neutrophils that were contacted with a fusion polypeptide comprised of a TAT polypeptide and the amino terminal SNARE domain of SNAP-23 (TAT-SNAP-23).
Figure 19:
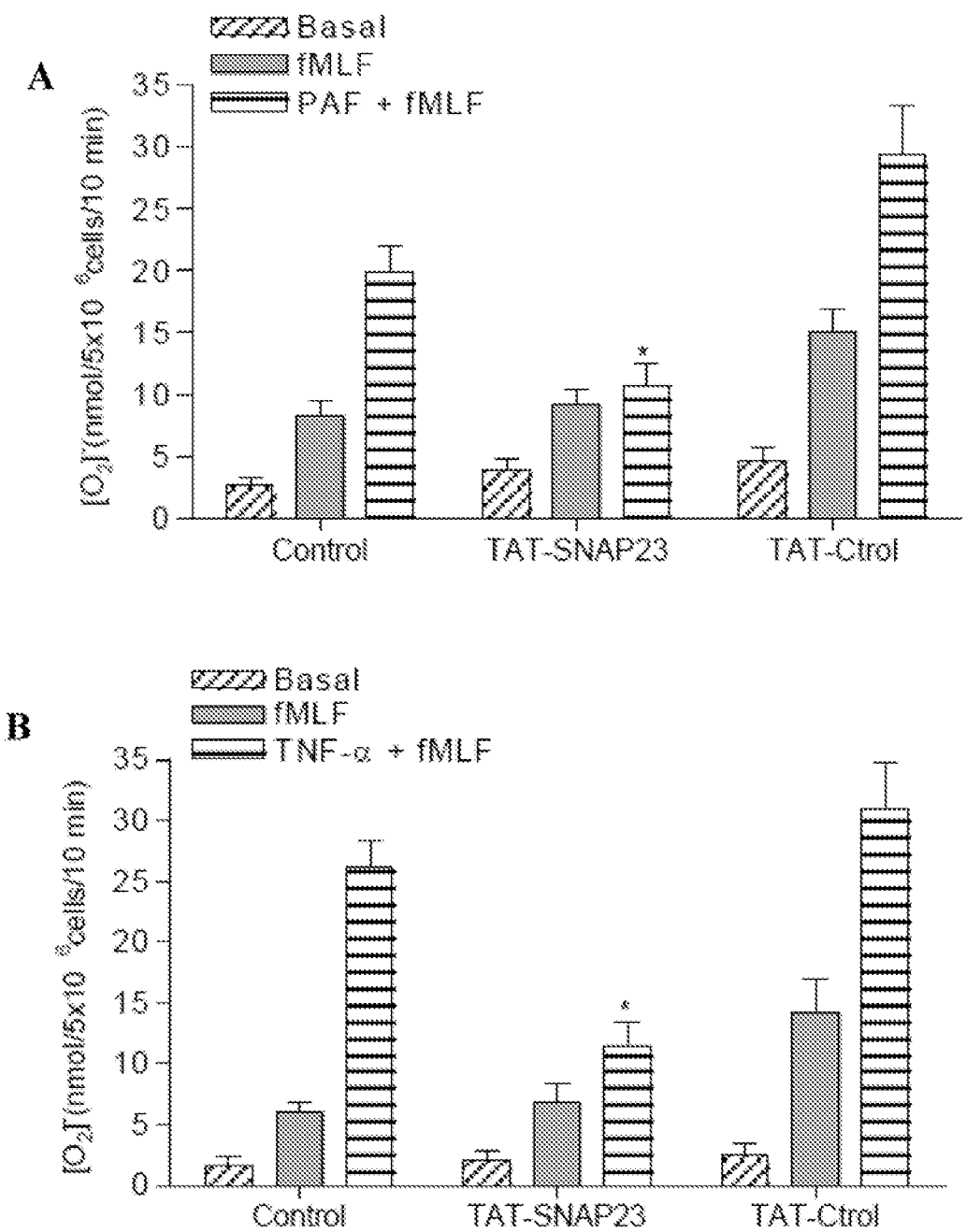
FIG. 19 includes graphs depicting the effect of a fusion polypeptide comprised of a TAT polypeptide and the amino terminal SNARE domain of SNAP-23 (TAT-SNAP-23) on superoxide release and priming of human neutrophils, where the neutrophils were primed with PAF (FIG. 19A) or TNFα (FIG. 19B) or left unprimed, and then stimulated with 300 nM fMLF.

The effect of TAT-SNAP-23 on exocytosis and priming of fMLP-stimulated superoxide release by PAF or TNFα is shown in FIGS. 18 and 19. Neutrophils were incubated with 0.8 µg/ml TAT-SNAP-23 or TAT-control for 10 min, then PAF (100 nM) or TNFα (2 ng/ml) was added for an additional 10 min. FIG. 18 shows that TAT-SNAP-23 significantly inhibited exocytosis of secretory vesicles (CD35) and specific granules (CD66b) stimulated by PAF and TNFα. To analyze priming, pre-treated neutrophils were incubated with or without 300 nM fMLF for 5 min, and superoxide release was measured. TAT-SNAP-23 had no effect on fMLF-stimulated superoxide release in unprimed neutrophils; however, TNFα- and PAF-mediated priming of respiratory burst activity was significantly inhibited by TAT-SNAP-23 (FIGS. 19A and 19B, respectively). These results thus indicate that exocytosis contributes to priming of respiratory burst activity by TNFα and PAF.

Figure 20:
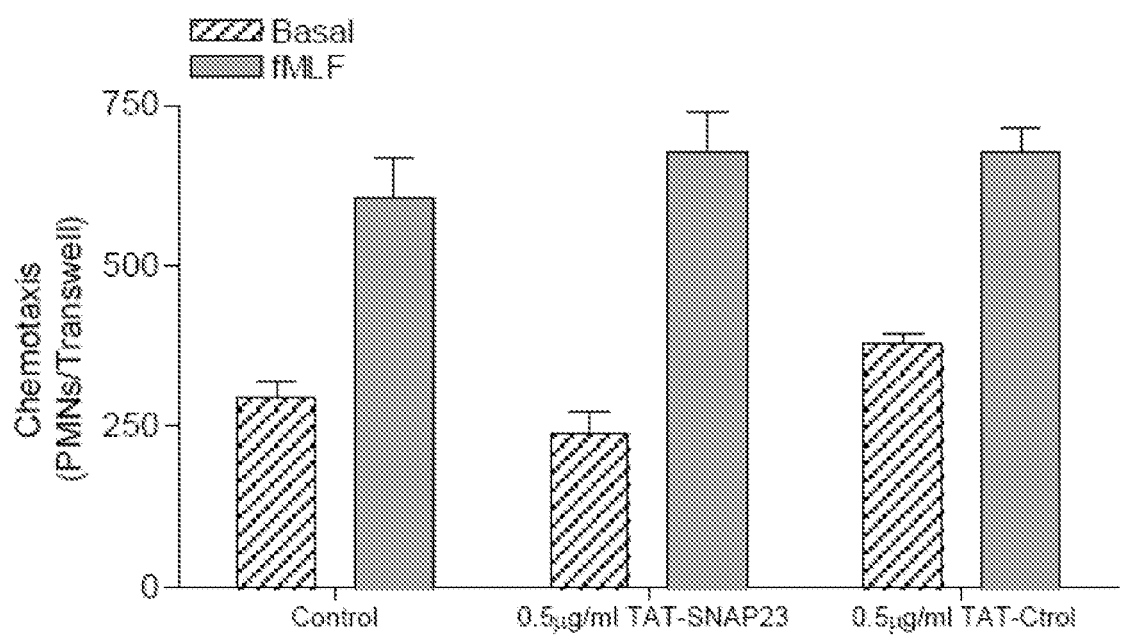
FIG. 20 is a graph depicting the effect of exocytosis inhibition on fMLF-stimulated chemotaxis, where the extent of chemotaxis (y-axis) is plotted against the various experimental groups (x-axis).

The effect of TAT-SNAP-23 and TAT-Control on chemotaxis was also determined. Briefly, neutrophils were either untreated or pretreated for 10 min at 37° C. with the TAT-SNAP-23 or TAT-Control polypeptides and the fMLP-stimulated ($3 \times 10^{-8}$ M) migration across a FluoroBlok™ insert was measured, as described previously (40). The results of FIG. 20 show that inhibition of exocytosis had no effect on chemotaxis, which is consistent with the findings in in vivo lung injury that exudation of neutrophils was not affected.

Throughout this document, various references are mentioned. All such references are incorporated herein by reference, including the references set forth in the following list:

REFERENCES

1. Faurschou, M., and Borregaard, N. Neutrophil granules and secretory vesicles in inflammation. Microbes Infect. 5(14):1317-1327, 2003.
2. El-Benna, J., Dang, P. M-C., Gougerot-Pocidalo, M-A., and Elbim, C. Phagocyte NADPH oxidase: a multicomponent enzyme essential for host defenses. Arch Immunol Ther Exp 53:199-206, 2005.
3. Sheppard, F. R., Kelher, M. R., Moore, E. E., McLaughlin N. J. D., Banerjee, A., and Silliman C. C. Structural organization of the neutrophil NADPH oxidase: phosphorylation and translocation during priming and activation. J Leukoc Biol 78 (5):1025-1042, 2005.
4. Lominadze, G., Powell, D. W., Luerman, G. C., Link, A. J., Ward, R. A., and McLeish, K. R. Proteomic analysis of human neutrophil granules. Mol Cell Proteomics 4(10): 1503-1521, 2005.
5. Ward, R. A., Nakamura, M., and McLeish, K. R. Priming of the neutrophil respiratory burst involves p38 mitogen-activated protein kinase-dependent exocytosis of flavocytochrome b558-containing granules. J Biol Chem 275(47): 36713-36719, 2000.
6. Brown, G. E., Stewart, M. Q., Bissonnette, S. A., Elias, A. E. H., Wilkers, E., and Yaffe, M. B. Distinct ligand-dependent roles of p38 MAPK in priming and activation of the neutrophil NADPH oxidase. J Biol Chem 279(26):27059-27068, 2004.
7. McLeish, K. R., Knall, C., Ward, R. A., Gerwins, P., Coxon, P. Y., Klein, J. B., and Johnson, G. L. Activation of mitogen-activated protein kinase cascades during priming of human neutrophils by TNF-α and GM-CSF. J Leukoc Biol 64:537-545, 1998.
8. Chen, Y. A., and Scheller, R. H. SNARE-mediated membrane fusion. Nat Rev Mol Cell Biol 2(2):98-106, 2001.
9. Hong, W. SNAREs and traffic. Biochimica et Biophysica Acta 1744: 120-144, 2005.
10. Burgoyne, R. D., and Morgan, A. Secretory granule exocytosis. Physiol Rev 83: 581-632, 2003.
11. Shukla, A., Corydon, T. J., Nielsen, S., Hoffmann, H. J., and Dahl, R. Identification of three new splice variants of the SNARE protein SNAP-23. Biochem Biophys Res Commun 285(2):320-327, 2001.
12. Mollinedo, F., and Lazo, P. A. Identification of two isoforms of the vesicle-membrane fusion protein SNAP-23 in human neutrophils and HL-60 cells. Biochem Biophys Res Commun 231: 808-812, 1997.
13. Martin-Martin, B., Nabokina, S. M., Blasi, J., Lazo, P. A., and Mollinedo, F. Involvement of SNAP-23 and syntaxin 6 in human neutrophil exocytosis. Blood 96: 2574-2583, 2000.
14. Mollinedo, F., Martin-Martin, B., Calafat, J., Nabokina, S. M., and Lazo, P. A. Role of Vesicle-Associated Membrane Protein-2, through Q-soluble N-ethylmaleimide-sensitive factor attachment protein receptor/R-soluble N-ethylmaleimide-sensitive factor attachment protein receptor interaction, in the exocytosis of specific and tertiary granules of human neutrophils. J Immunol. 170:1034-1042, 2003.
15. Rea, S., Martin, L. B., McIntosh, S., Macaulay, S. L., Ramsdale, T., Baldini, G., and James, D. E. Syndet, an adipocyte target SNARE involved in the insulin-induced translocation of GLUT4 to the cell surface. J Biol Chem 273(30):18784-18792, 1998.

16. Vaidyanathan, V. V., Puri, N., and Roche, P. A. The last exon of SNAP-23 regulates granule exocytosis from mast cells. J Biol Chem 276(27):25101-25106, 2001.
17. Matsushita, K., Morrell, C. N., and Lowenstein, C. J. A novel class of fusion polypeptides inhibits exocytosis. Molec Pharmacol 67(4):1137-1144, 2005.
18. Lominadze, G., Rane, M. J., Merchant, M., Cai, J., Ward, R. A., and McLeish, K. R. Myeloid-related protein-14 is a p38 MAPK substrate in human neutrophils. J Immunol. 174:7257-7267, 2005.
19. Rane, M. J., Gozal, D., Butt, W., Gozal, E., Pierce, W. M., Guo, S. Z., Wu, R., Goldbart, A. D., Thongboonkerd, V., McLeish, K. R., and Klein, J. B. γ-Amino butyric acid type B receptors stimulate neutrophil chemotaxis during ischemia-reperfusion. J Immunol. 174:7242-7249, 2005.
20. Coxon, P. Y., Rane, M. J., Powell, D. W., Klein, J. B., and McLeish, K. R. Differential mitogen-activated protein kinase stimulation by Fc gamma receptor IIa and Fc gamma receptor IIIb determines the activation phenotype of human neutrophils. J Immunol 164:6530-6537, 2000.
21. Rane, M. J., Pan, Y., Singh, S., Powell, D. W., Wu, R., Cummins, T., Chen, Q., McLeish, K. R., and Klein, J. B. Heat shock protein 27 controls apoptosis by regulating Akt activation. J Biol Chem 278:27828-27835, 2003.
22. Coxon, P. Y., Rane, M. J., Uriarte, S., Powell, D. W., Singh, S., Butt, W., Chen, Q., and McLeish, K. R. MAPK-activated protein kinase-2 participates in p38 MAPK-dependent and ERK-dependent functions in human neutrophils. Cell Signal 15(11): 993-1001, 2003.
23. Powell, D. W., Rane, M. J., Joughin, B. A., Kalmukova, R., Hong, J-H., Tidor, B., Dean, W. L., Pierce, W. M., Klein, J. B., Yaffe, M. B., and McLeish, K. R. Proteomic identification of 14-3-3ζ as a mitogen-activated protein kinase-activated protein kinase 2 substrate: role of dimmer formation and ligand binding. Mol Cell Biol 23(15):5376-5387, 2003.
24. Rane, M. J., Coxon, P. Y., Powell, D. W., and McLeish, K. R. Regulation of neutrophils functions by mitogen-activated protein kinase modules. Curr Topics Biochem Res 2:199-205, 2000.
25. Wadia, J. S., Stan, R. V., and Dowdy, S. F. Transducible TAT-HA fusogenic peptide enhances escape of TAT-fusion proteins after lipid raft macropinocytosis. Nat Med 10(3): 310-315, 2004.
26. Schwarze, S. R., Ho, A., Vocero-Akbani, A., and Dowdy, S. F. In vivo protein transduction: delivery of a biologically active protein into the mouse. Science 285 (5433):1569-1572, 1999.
27. Han, H., Fuortes, M., and Nathan, C. Critical role of the carboxyl terminus of praline-rich tyrosine kinases (Pyk2) in the activation of human neutrophils by tumor necrosis factor: separation of signals for the respiratory burst and degranulation. J Exp Med 197: 63-75, 2003.
28. Prochiantz, A. Messenger proteins: homeoproteins, TAT and others. Curr Opin Cell Biol 12: 400-406, 2000.
29. Gozal, E., Gozal, D., Pierce, W. M., Thongboonkerd, V., Scherzer, J. A., Sachleben, L. R. Jr., Guo, S-Z., and Klein, J. B. Proteomic analysis of CA1 and CA3 regions of rat hippocampus and differential susceptibility to intermittent hypoxia. Neurochemistry 83: 331-345, 2002.
30. Choi, M., Rolle, S., Wellner, M., Cardoso, M. C., Scheidereti, C., Luft, F. C., and Kettritz, R Inhibition of NF-kappaB by a TAT-NEMO-binding domain peptide accelerates constitutive apoptosis and abrogates LPS-delayed neutrophil apoptosis. Blood 102, 2259-2267, 2003.
31. Teng, F. Y., Wang, Y., and Tang, B. L. The syntaxins. Genome Biol 2 (11):Reviews 3012, 2001.
32. Dewas, C., Dang, P. M-C., Gougerot-Pocidalo, M-A., and El-Benna, J. TNF-α induces phosphorylation of p47phox in human neutrophils: Partial phosphorylation of p47phox is a common event of priming of human neutrophils by TNF-α and Granulocyte-Macrophage Colony-Stimulating Factor. J Immunol. 171:4392-4398, 2003.
33. Nakamura, M., Murakami, M., Koga, T., Tanaka, Y., and Minakami, S. Monoclonal antibody 7D5 raised to cytochrome b558 of human neutrophils: immunocytochemical detection of the antigen in peripheral phagocytes of normal subjects, patients with chronic granulomatous disease, and their carrier mothers. Blood 69(5):1404-1408, 1987.
34. Haslett, C., Guthrie, L., Kopaniak, M., Johnston, J., and Henson, P. Modulation of multiple neutrophils functions by preparative methods or trace concentrations of bacterial lipopolysaccharide. Am J Pathol 119:101-110, 1985.
35. Uriarte, S. M., Joshi-Barve, S., Song, Z., Sahoo, R., Gobejishvili, L., Jala, V. R., Haribabu, B., McClain, C., and Barve, S. Akt inhibition upregulates FasL, downregulates c-FLIPs and induces caspase-8 dependent cell death in Jurkat T lymphocytes. Cell Death and Differentiation (3): 233-242, 2005.
36. Lu, X., Garfield, A., Rainger, G. E., Savage, C. O. S., Nash, G. B., Mediation of endothelial cell damage by serine proteases, but not superoxide, released from antineutrophil cytoplasmic antibody-stimulated neutrophils. *Arthritis Rheum* 54:1619-1628, 2006.
37. Guo, R. F., Lentsch, A. B., Sarma, J. V., Sun, L., Riedemann, N. C., McClintock, S. D., McGuire, S. R., Rooijen, N. V., and Ward, P. A. Activator protein-1 activation in acute lung injury. *Am J Pathol* 161:275-282, 2002.
38. Lentsch, A. B., Czermak, B. J., Jordan, J. A., and Ward, P. A. Regulation of acute lung inflammatory injury by endogenous IL-13. *J Immunol* 162:1071-1076, 1999.
39. Mulligan, M. S., Varani, J., Warren, J. S., Till, G. O., Smith, C. W., Anderson, D. C., Todd, R. F., and Ward, P. A. Role of B2 integrins of rat neutrophils in complement- and oxygen radical-mediated acute inflammatory injury. J Immunol 148:1847-1857, 1992.
40. Coxon, P. Y., Rane, M. J., Uriarte, S., Powell, D. W., Singh, S., Chen, Q., and McLeish, K. R. MAPK-activated protein kinase-2 participates in p38-dependent- and ERK-dependent functions in human neutrophils. *Cell. Signal.* 15: 993-1001, 2003.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An isolated nucleic acid comprising the sequence of SEQ ID NO: 11.

2. A vector comprising the isolated nucleic acid of claim 1.

3. The vector of claim 2, wherein the isolated nucleic acid is operatively linked to an expression cassette.

4. An isolated cell comprising the nucleic acid sequence of claim 1.

5. An isolated fusion protein comprising the sequence of SEQ ID NO: 12.

6. An isolated cell comprising a nucleic acid sequence encoding a fusion protein comprising the sequence of SEQ ID NO: 12.

* * * * *

SEQUENCE LISTING

<160> NUMBER OF SEQ ID NOS: 18

<210> SEQ ID NO 1
<211> LENGTH: 78

```
<212> TYPE: PRT
<213> ORGANISM: Homo sapiens

<400> SEQUENCE: 1

Met Asp Asn Leu Ser Ser Glu Glu Ile Gln Gln Arg Ala His Gln Ile
1               5                   10                  15

Thr Asp Glu Ser Leu Glu Ser Thr Arg Arg Ile Leu Gly Leu Ala Ile
            20                  25                  30

Glu Ser Gln Asp Ala Gly Ile Lys Thr Ile Thr Met Leu Asp Glu Gln
        35                  40                  45

Lys Glu Gln Leu Asn Arg Ile Glu Gly Leu Asp Gln Ile Asn Lys
    50                  55                  60

Asp Met Arg Glu Thr Glu Lys Thr Leu Thr Glu Leu Asn Lys
65                  70                  75

<210> SEQ ID NO 2
<211> LENGTH: 40
<212> TYPE: PRT
<213> ORGANISM: Homo sapiens

<400> SEQUENCE: 2

Thr Ile Thr Met Leu Asp Glu Gln Lys Glu Gln Leu Asn Arg Ile Glu
1               5                   10                  15

Glu Gly Leu Asp Gln Ile Asn Lys Asp Met Arg Glu Thr Glu Lys Thr
            20                  25                  30

Leu Thr Glu Leu Asn Lys Cys Cys
        35                  40

<210> SEQ ID NO 3
<211> LENGTH: 60
<212> TYPE: PRT
<213> ORGANISM: Homo sapiens

<400> SEQUENCE: 3

Met Glu Glu Asn Leu Thr Gln Val Gly Ser Ile Leu Gly Asn Leu Lys
1               5                   10                  15

Asp Met Ala Leu Asn Ile Gly Asn Glu Ile Asp Ala Gln Asn Pro Gln
            20                  25                  30

Ile Lys Arg Ile Thr Asp Lys Ala Asp Thr Asn Arg Asp Arg Ile Asp
        35                  40                  45

Ile Ala Asn Ala Arg Ala Lys Lys Leu Ile Asp Ser
    50                  55                  60

<210> SEQ ID NO 4
<211> LENGTH: 24
<212> TYPE: PRT
<213> ORGANISM: Homo sapiens

<400> SEQUENCE: 4

Thr Asp Lys Ala Asp Thr Asn Arg Asp Arg Ile Asp Ile Ala Asn Ala
1               5                   10                  15

Arg Ala Lys Lys Leu Ile Asp Ser
            20

<210> SEQ ID NO 5
<211> LENGTH: 11
<212> TYPE: PRT
<213> ORGANISM: Human immunodeficiency virus

<400> SEQUENCE: 5

Tyr Gly Arg Lys Lys Arg Arg Gln Arg Arg Arg
```

-continued

<210> SEQ ID NO 6
<211> LENGTH: 16
<212> TYPE: PRT
<213> ORGANISM: Drosophila melanogaster

<400> SEQUENCE: 6

Ala Lys Ile Trp Phe Gln Asn Arg Arg Met Lys Trp Lys Lys Glu Asn
1               5                   10                  15

<210> SEQ ID NO 7
<211> LENGTH: 301
<212> TYPE: PRT
<213> ORGANISM: human herpesvirus 1

<400> SEQUENCE: 7

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Pro Val Glu
290                 295                 300

<210> SEQ ID NO 8

-continued

```
<211> LENGTH: 9
<212> TYPE: PRT
<213> ORGANISM: Artificial Sequence
<220> FEATURE:
<223> OTHER INFORMATION: Synthetic sequence

<400> SEQUENCE: 8

Arg Arg Arg Arg Arg Arg Arg Arg Arg
1               5

<210> SEQ ID NO 9
<211> LENGTH: 21
<212> TYPE: PRT
<213> ORGANISM: Simian virus 40

<400> SEQUENCE: 9

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 10
<211> LENGTH: 27
<212> TYPE: PRT
<213> ORGANISM: Artificial Sequence
<220> FEATURE:
<223> OTHER INFORMATION: Transportan cell-penetrating peptide

<400> SEQUENCE: 10

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 11
<211> LENGTH: 438
<212> TYPE: DNA
<213> ORGANISM: Artificial Sequence
<220> FEATURE:
<223> OTHER INFORMATION: TAT-hemagglutinin-SNAP 23 aptamer

<400> SEQUENCE: 11
atgcggggtt ctcatcatca tcatcatcat ggtatggcta gcatgactgg tggacagcaa      60
atgggtcggg atctgtacga cgatgacgat aaggatcgat ggggatccaa gcttggctac     120
ggccgcaaga aacgccgcca gcgccgccgc ggtggatcca ccatgtccgg ctatccatat     180
gacgtcccag actatgctgg ctccatggat aatctgtcat cagaagaaat tcaacagaga     240
gctcaccaga ttactgatga gtctctggaa agtacgagga gaatcctggg tttagccatt     300
gagtctcagg atgcaggaat caagaccatc actatgctgg atgaacaaaa ggaacaacta     360
aaccgcatag aagaaggctt ggaccaaata aataaggaca tgagagagac agagaagact     420
ttaacagaac tcaacaaa                                                    438

<210> SEQ ID NO 12
<211> LENGTH: 146
<212> TYPE: PRT
<213> ORGANISM: Artificial Sequence
<220> FEATURE:
<223> OTHER INFORMATION: TAT-Hemagglutinin-SNAP-23 aptamer

<400> SEQUENCE: 12

Met Arg Gly Ser His His His His His His Gly Met Ala Ser Met Thr
1               5                   10                  15
```

Gly Gly Gln Gln Met Gly Arg Asp Leu Tyr Asp Asp Asp Lys Asp
            20                  25                  30

Arg Trp Gly Ser Lys Leu Gly Tyr Gly Arg Lys Lys Arg Gln Arg
        35                  40                  45

Arg Arg Gly Gly Ser Thr Met Ser Gly Tyr Pro Tyr Asp Val Pro Asp
50                  55                  60

Tyr Ala Gly Ser Met Asp Asn Leu Ser Ser Glu Glu Ile Gln Gln Arg
65                  70                  75                  80

Ala His Gln Ile Thr Asp Glu Ser Leu Glu Ser Thr Arg Arg Ile Leu
                85                  90                  95

Gly Leu Ala Ile Glu Ser Gln Asp Ala Gly Ile Lys Thr Ile Thr Met
            100                 105                 110

Leu Asp Glu Gln Lys Glu Gln Leu Asn Arg Ile Glu Glu Gly Leu Asp
        115                 120                 125

Gln Ile Asn Lys Asp Met Arg Glu Thr Glu Lys Thr Leu Thr Glu Leu
    130                 135                 140

Asn Lys
145

<210> SEQ ID NO 13
<211> LENGTH: 9
<212> TYPE: PRT
<213> ORGANISM: Homo sapiens

<400> SEQUENCE: 13

Tyr Pro Tyr Asp Val Pro Asp Tyr Ala
1               5

<210> SEQ ID NO 14
<211> LENGTH: 27
<212> TYPE: DNA
<213> ORGANISM: Artificial Sequence
<220> FEATURE:
<223> OTHER INFORMATION: Forward RT-PCR Primer for amplifying a
      full-length SNAP-23 sequence

<400> SEQUENCE: 14
cttgagtttt gattcaccat ggataat                                        27

<210> SEQ ID NO 15
<211> LENGTH: 27
<212> TYPE: DNA
<213> ORGANISM: Artificial Sequence
<220> FEATURE:
<223> OTHER INFORMATION: Reverse RT-PCR Primer for amplifying a
      full-length SNAP-23 sequence

<400> SEQUENCE: 15
gaagtgaata agctttaaag aagaaca                                        27

<210> SEQ ID NO 16
<211> LENGTH: 28
<212> TYPE: DNA
<213> ORGANISM: Artificial Sequence
<220> FEATURE:
<223> OTHER INFORMATION: Reverse RT-PCR Primer for amplifying an amino
      terminus SNAP-23 sequence

<400> SEQUENCE: 16
cagacacaaa gcttacatca tttgttga                                       28

<210> SEQ ID NO 17
<211> LENGTH: 24

```
<212> TYPE: DNA
<213> ORGANISM: Artificial Sequence
<220> FEATURE:
<223> OTHER INFORMATION: Forward RT-PCR Primer for amplifying a carboxy
      terminus SNAP-23 sequence

<400> SEQUENCE: 17
agagaagatg ccatggaaga gaac                                            24

<210> SEQ ID NO 18
<211> LENGTH: 68
<212> TYPE: PRT
<213> ORGANISM: Homo sapiens

<400> SEQUENCE: 18

Val Thr Arg Gln Ala Leu Asn Glu Ile Ser Ala Arg His Ser Glu Ile
1               5                   10                  15

Gln Gln Leu Glu Arg Ser Ile Arg Glu Leu His Asp Ile Phe Thr Phe
            20                  25                  30

Leu Ala Thr Glu Val Glu Met Gln Gly Glu Met Ile Asn Arg Ile Glu
        35                  40                  45

Lys Asn Ile Leu Ser Ser Ala Asp Tyr Val Glu Arg Gly Gln Glu His
    50                  55                  60

Val Lys Thr Ala
65
```